United States Patent
Park et al.

(10) Patent No.: US 10,405,814 B2
(45) Date of Patent: Sep. 10, 2019

(54) X-RAY IMAGING APPARATUS AND METHOD FOR GENERATING PANORAMIC IMAGE USING THE SAME

(71) Applicant: GENORAY CO., LTD., Seongnam-si, Gyeonggi-do (KR)

(72) Inventors: Byung Uk Park, Seoul (KR); Jin Hwan Jun, Anyang-si (KR); Chan Woo Hwang, Yongin-si (KR); Chang Yoon Lee, Yongin-si (KR); Gyu Jung Cho, Seongnam-si (KR)

(73) Assignee: GENORAY CO., LTD., Seongnam-si (KR)

( * ) Notice: Subject to any disclaimer, the term of this patent is extended or adjusted under 35 U.S.C. 154(b) by 303 days.

(21) Appl. No.: 15/228,441

(22) Filed: Aug. 4, 2016

(65) Prior Publication Data

US 2017/0224292 A1    Aug. 10, 2017

(30) Foreign Application Priority Data

Feb. 4, 2016  (KR) .................. 10-2016-0014502
Feb. 4, 2016  (KR) .................. 10-2016-0014503
Feb. 4, 2016  (KR) .................. 10-2016-0014504

(51) Int. Cl.
*A61B 6/14*     (2006.01)
*A61B 6/03*     (2006.01)
(Continued)

(52) U.S. Cl.
CPC ............. *A61B 6/14* (2013.01); *A61B 6/027* (2013.01); *A61B 6/032* (2013.01); *A61B 6/035* (2013.01); *A61B 6/542* (2013.01)

(58) Field of Classification Search
CPC ...... A61B 6/14; A61B 6/032; G06T 2211/412
See application file for complete search history.

(56) References Cited

U.S. PATENT DOCUMENTS

| 2009/0041191 A1* | 2/2009 | Suzuki | A61B 6/14 378/98.5 |
| 2009/0196395 A1* | 8/2009 | Gregorio | A61B 6/14 378/38 |
| 2011/0064188 A1* | 3/2011 | Suzuki | A61B 6/14 378/21 |

FOREIGN PATENT DOCUMENTS

| JP | 2009-531104 A | 9/2009 |
| JP | 2014-094091 A | 5/2014 |

(Continued)

OTHER PUBLICATIONS

Office Action dated Dec. 11, 2016, issued in counterpart Korean Application No. 10-2016-0014502. (11 pages).

(Continued)

*Primary Examiner* — Kenneth J Malkowski
(74) *Attorney, Agent, or Firm* — Westerman, Hattori, Daniels & Adrian, LLP

(57) ABSTRACT

An X-ray imaging apparatus according to an embodiment of the present invention includes an X-ray generator that irradiates an object with X-rays during an exposure period; an X-ray detector that detects X-rays transmitted through the object; and a movement unit that moves the X-ray generator and the X-ray detector, wherein the X-ray generator is moved along an arc having a radius of curvature within a range with respect to a rotational axis, wherein the motion along the arc starts at a first time point and ends at a second time point, wherein the X-ray detector is moved in a linear direction having an angle with respect to a plane of the arc during at least a partial period of a period between the first time point and the second time point, wherein the motion in a linear direction starts at a third time point that is the same as or later than the first time point and ends at a fourth time point that is the same as or earlier than the second time point, and a first difference between the first time point and the (Continued)

second time point is larger than or equal to a second difference between the third time point and the fourth time point.

17 Claims, 14 Drawing Sheets

(51) Int. Cl.
  *A61B 6/02*  (2006.01)
  *A61B 6/00*  (2006.01)

(56) References Cited

FOREIGN PATENT DOCUMENTS

| | | | |
|---|---|---|---|
| KR | 10-2009-0054447 | A | 5/2000 |
| KR | 10-2009-0077025 | A | 7/2009 |
| KR | 10-0929357 | B1 | 12/2009 |
| KR | 10-2010-0011300 | A | 2/2010 |
| KR | 10-2010-0090595 | A | 8/2010 |
| KR | 10-2010-0120810 | A | 11/2010 |
| KR | 10-1000315 | B1 | 12/2010 |
| WO | 2015/092119 | A1 | 6/2015 |

OTHER PUBLICATIONS

Office Action dated Dec. 11, 2016, issued in counterpart Korean Application No. 10-2016-0014503. (8 pages).
Notice of Allowance dated Mar. 3, 2017, issued in Korean Application No. 10-2016-0014502. (2 pages).

* cited by examiner

X-RAY IMAGING APPARATUS AND METHOD FOR GENERATING PANORAMIC IMAGE USING THE SAME

CROSS-REFERENCE TO RELATED APPLICATION

This application claims priority to and the benefit of Korean Patent Application Nos. 10-2016-0014502, 10-2016-0014503 and 10-2016-0014504 filed on Feb. 4, 2016 the disclosure of which is incorporated herein by reference in its entirety.

BACKGROUND

1. Field of the Invention

The present invention relates to an X-ray imaging apparatus, and more particularly, to a method for generating a panoramic image using the same.

2. Discussion of Related Art

In dental clinics, conventionally, a method for imaging a panoramic image by imaging an overall structure of a tooth and an alveolar bone using an X-ray imaging apparatus for dentistry during treatment or straightening of irregular teeth, a method for taking a cephalo image which is taken from the front side of a head and maxillary bone areas of a patient to the rear side thereof from the rear side thereof to the front side thereof and from the left side thereof to right side thereof, a method for inserting a small sensor for receiving an X-ray beam into an oral cavity of a patient and irradiating the sensor with the X-ray beam with a narrow width outside an oral cavity, and the like have been utilized.

Among these, the method for imaging a panoramic image can observe overall areas of a tooth and an alveolar bone in a planar view and reduce an X-ray exposure dose to a patient, and thereby may be widely used.

In a conventional panoramic imaging apparatus, an X-ray generator and an X-ray detector may be configured to face each other. Here, the X-ray generator may irradiate the head of a patient with X-rays by rotating the panoramic imaging apparatus, and the panoramic imaging apparatus may detect the X-rays transmitted by the X-ray detector to generate a panoramic image.

The conventional panoramic imaging apparatus may perform X-ray radiography using an X-ray detector larger than a dental arch of a patient in order to image all of curved dental arches of the patient so that unnecessary X-ray exposure may occur, and the use of the large-sized X-ray detector may lead to an increase in manufacturing costs.

SUMMARY OF THE INVENTION

The present invention is directed to an X-ray imaging apparatus that can reduce an X-ray exposure dose to a patient.

The present invention is directed to a method for generating a panoramic image that can reduce manufacturing costs.

According to an aspect of the present invention, there is provided an X-ray imaging apparatus including: an X-ray generator that irradiates an object with X-rays during an exposure period, an X-ray detector that detects X-rays transmitted through the object; and a movement unit that moves the X-ray generator and the X-ray detector, wherein the X-ray generator is moved along an arc having a radius of curvature within a range with respect to a rotational axis, wherein the motion along the arc starts at a first time point and ends at a second time point, wherein the X-ray detector is moved in a linear direction having an angle with respect to a plane of the arc during at least a partial period of a period between the first time point and the second time point, wherein the motion in a linear direction starts at a third time point that is the same as or later than the first time point and ends at a fourth time point that is the same as or earlier than the second time point, and a first difference between the first time point and the second time point is larger than or equal to a second difference between the third time point and the fourth time point.

According to another aspect of the present invention, there is provided an X-ray imaging apparatus comprising: an X-ray generator that generates X-rays during an exposure period; an optical path restricting unit that restricts an X-ray irradiation range from the X-ray generator, an X-ray detector that includes a light receiving area, wherein the light receiving area is determined an area of receiving X-rays transmitted through the object; and a movement unit that moves the X-ray generator and the X-ray detector, wherein the X-ray generator is moved along an arc having a radius of curvature within a range, wherein the motion along the arc starts at a first time point and ends at a second time point, wherein the light receiving area is moved in a linear direction having an angle with respect to a plane of the arc during at least a partial period of a period between the first time point and the second time point, wherein the motion in a linear direction starts at a third time point that is the same as or later than the first time point and ends at a fourth time point that is the same as or earlier than the second time point, and a first difference between the first time point and the second time point is larger than or equal to a second difference between the third time point and the fourth time point.

According to still another aspect of the present invention, there is provided an X-ray imaging apparatus comprising an X-ray generator that irradiates an object with X-rays during an exposure period; an X-ray detector that detects X-rays transmitted through the object; and a movement unit that moves the X-ray generator and the X-ray detector, wherein the X-ray generator is moved along an arc having a radius of curvature within a range, and a motion along the arc starts at a first time point and ends at a second time point, when a first mode between the first mode and a second mode is set, the X-ray detector is moved in a linear direction having a angle with respect to a plane of the arc during at least a partial period of a period between the first time point and the second time point, and when the second mode between the first mode and the second mode is set, the X-ray generator and the X-ray detector is moved along the arc having a radius of curvature within the range, wherein the motion in a linear direction starts at a third time point that is the same as or later than the first time point and ends at a fourth time point that is the same as or earlier than the second time point, and a first difference between the first time point and the second time point may be larger than or equal to a second difference between the third time point and the fourth time point.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 1 is a block diagram illustrating a system that includes an X-ray imaging apparatus according to embodiments of the present invention, an electronic device that works with the X-ray imaging apparatus, and the like;

DETAILED DESCRIPTION OF EXEMPLARY EMBODIMENTS

Figure 1:
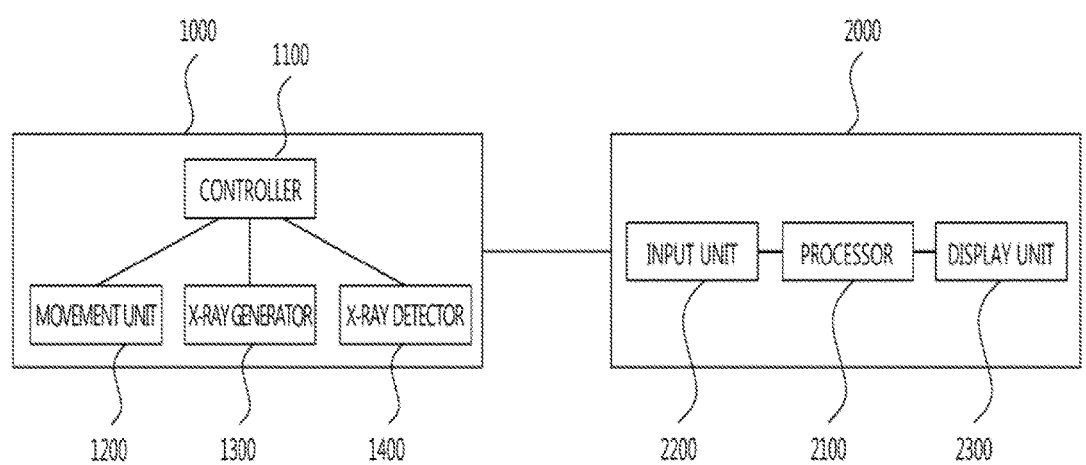

Exemplary embodiments of the present invention will be described in detail below with reference to the accompanying drawings. While the present invention is shown and described in connection with exemplary embodiments thereof, it should be apparent to those skilled in the art that various modifications can be made without departing from the spirit and scope of the invention.

In addition, it should be noted that the same reference numerals throughout the specification refer to like elements.

According to an aspect of the present invention, there is provided an X-ray imaging apparatus including: an X-ray generator that irradiates an object with X-rays during an exposure period; an X-ray detector that detects X-rays transmitted through the object; and a movement unit that moves the X-ray generator and the X-ray detector, wherein the X-ray generator is moved along an arc having a radius of curvature within a range with respect to a rotational axis, wherein the motion along the arc starts at a first time point and ends at a second time point, wherein the X-ray detector is moved in a linear direction having an angle with respect to a plane of the arc during at least a partial period of a period between the first time point and the second time point, wherein the motion in a linear direction starts at a third time point that is the same as or later than the first time point and ends at a fourth time point that is the same as or earlier than the second time point, and a first difference between the first time point and the second time point is larger than or equal to a second difference between the third time point and the fourth time point.

The exposure period may start earlier than the first time point and end later than the second time point.

The exposure period may start later than the first time point and end earlier than the second time point.

The exposure period may start earlier than the first time point and end earlier than the second time point.

The exposure period may start later than the first time point and end later than the second time point.

The exposure period may be the same as the first difference.

The arc may be predefined.

The X-ray detector may be used for computed tomography (CT).

The linear motion of the X-ray detector may be a reciprocating motion between a first position and a second position.

The X-ray detector is moved from the first position to the second position during a first linear motion, the linear motion being started at the third time point and being ended at a fifth time point, and the X-ray detector is moved from the second position to the first position during a second linear motion, the second linear motion being started at a sixth time point and being ended at the fourth time point.

The fifth time point and the sixth time point may be the same time point.

The X-ray detector may be located at the second position between the fifth time point and the sixth time point and detect X-rays transmitted through a lowest end of a region of interest between the fifth time point and the sixth time point.

The X-ray generator may irradiate X-rays so that they to correspond to the location of the X-ray detector.

The X-ray generator is moved in a linear direction between the third time point and the fourth time point.

The X-ray imaging apparatus according to an embodiment of the present invention may further include an optical path restricting unit that is located between the X-ray generator and the object and restricts an X-ray irradiation range from the X-ray generator so that X-rays are controlled to be output toward a specific region of the object.

The optical path restricting unit may control a light receiving area to be moved in a linear direction between the third time point and the fourth time point.

The X-ray imaging apparatus according to an embodiment of the present invention may further include a detector housing in which the X-ray detector is located, and the X-ray detector is moved in a linear motion by a linear motion of the detector housing.

The X-ray imaging apparatus according to an embodiment of the present invention may further include a linear movement unit that moves the detector housing linearly.

The X-ray generator and the X-ray detector may move while maintaining a state in which they face each other.

The X-ray detector may be movable in a vertical direction with respect to the X-ray generator.

An X-ray irradiation range may be restricted so that is corresponds to the movement of the X-ray detector.

An X-ray imaging apparatus according to another embodiment of the present invention is characterized in that it includes an X-ray generator that generates X-rays during an exposure period; an optical path restricting unit that restricts an X-ray irradiation range from the X-ray generator; an X-ray detector that includes a light receiving area, wherein the light receiving area is determined an area of receiving X-rays transmitted through the object; and a movement unit that moves the X-ray generator and the X-ray detector, wherein the X-ray generator is moved along an arc having a radius of curvature within a range, wherein the motion along the arc starts at a first time point and ends at a second time point, wherein the light receiving area is moved in a linear direction having an angle with respect to a plane of the arc during at least a partial period of a period between the first time point and the second time point, wherein the motion in a linear direction starts at a third time point that is the same as or later than the first time point and ends at a fourth time point that is the same as or earlier than the second time point, and a first difference between the first time point and the second time point is larger than or equal to a second difference between the third time point and the fourth time point.

An area of the light receiving area may be smaller than an area of the X-ray detector.

The X-ray detector may include a first boundary surface and a second boundary surface that face each other, wherein a distance between a first side of the light receiving area, which is adjacent to the first boundary surface, and the first boundary surface may be smaller than a distance between a second side of the light receiving area, which is adjacent to the second boundary surface, and the second boundary surface during the first time point to the third time point.

The X-ray detector may include the first boundary surface and the second boundary surface that face each other, the distance between the first side of the light receiving area, which is adjacent to the first boundary surface, and the first boundary surface may be larger than the distance between the second side of the light receiving area, which is adjacent to the second boundary surface, and the second boundary surface during a partial period between the third time point and the fourth time point.

The motion in the linear direction of the light receiving area may be a reciprocating motion between a first position and a second position.

The light receiving area is moved from the first position to the second position during a first linear motion, the first linear motion being started at the third time point and being ended at a fifth time point, the light receiving area is moved from the second position to the first position during a second linear motion, the second linear motion being started at a sixth time point and being ended at a fourth time point.

The X-ray detector may include the first boundary surface and the second boundary surface that face each other, the distance between the first side of the light receiving area, which is adjacent to the first boundary surface, and the first boundary surface may be increased, and the distance between the second side of the light receiving area, which is adjacent to the second boundary surface, and the second boundary surface may be decreased during the third time point to the fifth time point.

The X-ray detector may include the first boundary surface and the second boundary surface that face each other, the distance between the first side of the light receiving area, which is adjacent to the first boundary surface, and the first boundary surface may be decreased, and the distance between the second side of the light receiving area, which is adjacent to the second boundary surface, and the second boundary surface may be increased during the sixth time point to the fourth time point.

The light receiving area at a specific time point during the exposure period may be set to be different from the light receiving area at the specific time point during a previous exposure period.

An X-ray imaging apparatus according to the other embodiment of the present invention is characterized in that it includes an X-ray generator that irradiates an object with X-rays during an exposure period; an X-ray detector that detects X-rays transmitted through the object; and a movement unit that moves the X-ray generator and the X-ray detector, wherein the X-ray generator is moved along an arc having a radius of curvature within a range, and a motion along the arc starts at a first time point and ends at a second time point, when a first mode between the first mode and a second mode is set, the X-ray detector is moved in a linear direction having a angle with respect to a plane of the arc during at least a partial period of a period between the first time point and the second time point, and when the second mode between the first mode and the second mode is set, the X-ray generator and the X-ray detector is moved along the arc having a radius of curvature within the range, wherein the motion in a linear direction starts at a third time point that is the same as or later than the first time point and ends at a fourth time point that is the same as or earlier than the second time point, and a first difference between the first time point and the second time point may be larger than or equal to a second difference between the third time point and the fourth time point.

A method for generating a panoramic image using an X-ray imaging apparatus according to an embodiment of the present invention is characterized in that it includes generating, by an X-ray generator, X-rays during an exposure period; restricting, by an optical path restricting unit, an X-ray irradiation range from the X-ray generator; and generating, by an X-ray detector including a light receiving area, wherein the light receiving area is determined an area of receiving X-rays, a plurality of frames. The X-ray generator is moved along an arc having a radius of curvature within a range, and at this point, a motion along the arc starts at a first time point and ends at a second time point. The light receiving area is moved in a linear direction having an angle with respect to a plane of the arc during at least a partial period of a period between the first time point and the second time point, and the motion in a linear direction starts at a third time point that is the same as or later than the first time point and ends at a fourth time point that is the same as or earlier than the second time point. At this point, a first difference between the first time point and the second time point is larger than or equal to a second difference between the third time point and the fourth time point.

A storage medium in which the method for generating a panoramic image using an X-ray imaging apparatus is stored may be provided.

An X-ray imaging apparatus according to further embodiment of the present invention is characterized in that it includes an X-ray generator that irradiates an object with X-rays during an exposure period; and an X-ray detector that generates a first frame by detecting X-rays transmitted through the object at a first time point during the exposure period and generates a second frame by detecting the X-rays transmitted through the object at a second time point during the exposure period. Here, each of the first frame and the second frame includes a plurality of pixels, and at least an outermost pixel column of the first frame, which is adjacent to the second frame, includes a first pixel group and a second pixel group adjacent to the first pixel group. At this point, the second frame includes a pixel corresponding to at least one pixel of the second pixel group and does not include a pixel corresponding to the first pixel group.

The second pixel group may be located below the first pixel group.

The second pixel group may be located above the first pixel group.

The pixel of the second frame corresponding to the pixel of the second pixel group of the first frame and the pixel of the second pixel group of the first frame may have the same pixel value.

An overlapped region that is defined by the second pixel group of the first frame and a plurality of pixels of the second frame corresponding to the second pixel group may be a region that is generated by detecting X-rays transmitted through the same region of the object.

The X-ray imaging apparatus according to further embodiment of the present invention may further include a movement unit that moves the X-ray generator and the X-ray detector, and the movement unit may move the X-ray generator and the X-ray detector so that the first frame and the second frame may have the overlapped region.

The X-ray detector may be used for CT.

The X-ray generator may be moved to draw an arc having a radius of curvature within a range with respect to a rotational axis, and the X-ray detector may perform a linear motion in a linear direction having an angle with respect to a plane where at least one circle having the radius of curvature is located during at least a partial period of a period during which the X-ray generator performs the motion to draw the arc.

The X-ray imaging apparatus according to further embodiment of the present invention may further include a detector housing in which the X-ray detector is located, the X-ray generator may be moved to draw the arc having a radius of curvature within the range with respect to the rotational axis, and the detector housing may perform a linear motion in the linear direction having an angle with respect to the plane where at least one circle having the radius of curvature is located during at least the partial period of the period during which the X-ray generator performs the motion to draw the are.

The X-ray generator may irradiate an X-ray to correspond to a location of the X-ray detector.

The X-ray imaging apparatus according to further embodiment of the present invention may further include an optical path restricting unit that is located between the X-ray generator and the object and restricts an X-ray irradiation range from the X-ray generator so that X-rays are controlled to be output toward a specific region of the object.

The X-ray generator may be moved to draw the arc having a radius of curvature within the range with respect to the rotational axis, and the optical path restricting unit may control a light receiving area to be moved in a linear direction having a angle with respect to the plane where at least one circle having the radius of curvature is located during at least the partial period of the period during which the X-ray generator performs the motion to draw the are.

An X-ray imaging apparatus according to further embodiment of the present invention includes an X-ray generator that irradiates an object with X-rays during an exposure period; and an X-ray detector that generates a first frame by detecting X-rays transmitted through the object at a first time point during the exposure period, generates a second frame by detecting the X-rays transmitted through the object at a second time point during the exposure period, generates a third frame by detecting the X-rays transmitted through the object at a third time point during the exposure period, and generates a fourth frame by detecting the X-rays transmitted through the object at a fourth time point during the exposure period. Here, each of the first frame, the second frame, the third frame, and the fourth frame may include a plurality of pixels, and at least an outermost pixel column of the first frame, which is adjacent to the second frame, may include a first pixel group and a second pixel group adjacent to the first pixel group. At this point, the second frame may include a pixel corresponding to at least one pixel of the second pixel group and may not include a pixel corresponding to the first pixel group, and at least an outermost pixel column of the third frame, which is adjacent to the fourth frame, may correspond to at least one pixel column of the fourth frame.

The X-ray detector may be reciprocally moved between a first position and a second position.

The X-ray detector located at the first position may start a first linear motion at a fifth time point and reach the second position at a sixth time point, and the X-ray detector located at the second position may start a second linear motion at a seventh time point and reach the first position at an eighth time point.

The third time point and the fourth time point may be time points that are earlier than the fifth time point or later than the eighth time point.

The third time point and the fourth time point may be time points between the sixth time point and the seventh time point.

The first time point and the second time point may be time points between the fifth time point and the sixth time point or between the seventh time point and the eighth time point.

A method for generating a panoramic image using an X-ray imaging apparatus according to further embodiment of the present invention includes irradiating an object with X-rays during an exposure period; generating a first frame by detecting X-rays transmitted through the object at a first time point during the exposure period; generating a second frame by detecting the X-rays transmitted through the object at a second time point during the exposure period; and generating a panoramic image using a plurality of frames including the first frame and the second frame. Here, each of the first frame and the second frame may include a plurality of pixels, and at least an outermost pixel column of the first frame, which is adjacent to the second frame, may include a first pixel group and a second pixel group adjacent to the first pixel group. At this point, the second frame may include a pixel corresponding to at least one pixel of the second pixel group, and the second frame may not include a pixel corresponding to the first pixel group.

A storage medium in which the method for generating a panoramic image using an X-ray imaging apparatus is stored may be provided.

An X-ray imaging apparatus according to further embodiment of the present invention includes an X-ray generator that irradiates an object with X-rays during an exposure period; an X-ray detector that generates a plurality of frames during at least a partial period of the exposure period by detecting the X-rays transmitted through the object; and a controller that generates a panoramic image by overlapping the plurality of frames transmitted from the X-ray detector. Here, the panoramic image may be generated in such a manner that the plurality of frames are overlapped and arranged along a reference line, and the reference line may include a first reference line region and a second reference line region. At this point, the first reference line region may be a reference for overlapping at least two frames generated between a first time point and a second time point, the second reference line region may be a reference for overlapping at least two frames generated between a third time point and a fourth time point, and the first reference line region and the second reference line region may have a different angle from each other with respect to a lower boundary line of the plurality of frames.

The first reference line region and the second reference line region may be consecutive regions.

The first reference line region and the second reference line region may be spatially spaced apart from each other.

The reference line may be a virtual reference line.

The central point of each of the frames may be arranged to be positioned on the reference line so that the panoramic image may be generated.

The central point of the frame may be a center of gravity of the frame.

The reference line may be a pre-defined line.

The reference line may be positioned to pass an ROI (region of interest) of the object.

The reference line of a partial region between the first reference line region and the second reference line region may be parallel to the lower boundary line of the plurality of frames by a selection of the first to fourth time points.

Absolute values of angles of the first reference line region and the second reference line region may be the same with respect to the lower boundary line of the plurality of frames by a selection of the first to fourth time points.

The reference line may include a left reference line region and a right reference line region with respect to a middle region of the panoramic image, and the middle region may be a region that is parallel to the lower boundary line of the plurality of frames.

The left reference line region may include a first region adjacent to the middle region, a second region spaced apart from the middle region, and a third region positioned between the first region and the second region. At this point, the first region may have a smaller absolute value of the angle of the reference line as it is closer to the middle region, and the third region may have a greater absolute value of the angle of the reference line as it is closer to the middle region.

The second region may have the same angle as the middle region.

The left reference line region and the right reference line region may be symmetric with respect to the middle region.

An X-ray imaging apparatus according to further embodiment of the present invention includes an X-ray generator that irradiates an object with X-rays during an exposure period; an X-ray detector that generates a plurality of frames during at least a partial period of the exposure period by detecting X-rays transmitted through the object; and a controller that generates a panoramic image by overlapping the plurality of frames transmitted from the X-ray detector. Here, the panoramic image may be generated in such a manner that the plurality of frames are overlapped and arranged along a reference line, and the reference line may be configured by connecting a plurality of reference lines including a first reference line and a second reference line. At this point, the first reference line may be a line that connects central points of a first frame at a first time point and a second frame at a second time point, the second reference line may be a line that connects central points of a third frame at a third time point and a fourth frame at a fourth time point, and the first reference line and the second reference line may have different inclinations.

The first frame and the second frame may be adjacent to each other, and the third frame and the fourth frame may be adjacent to each other.

The reference line may be predefined according to the type of object.

At least a part of each of the reference lines may be perpendicular relative to a side boundary line of each of the frames.

The X-ray imaging apparatus according to further embodiment of the present invention may further include a display unit that outputs an output image including the panoramic image, and a width of the output image may be larger than a width of the frame.

The output image may include a dummy region in which the frame is not arranged.

The dummy region may have a uniform gradation.

The output image may include a first boundary line and a second boundary line facing the first boundary line, a fifth frame at a fifth time point may meet the first boundary line and may not meet the second boundary line.

A sixth frame at a sixth time point may meet the second boundary line and may not meet the first boundary line.

A seventh frame at a seventh time point between the fifth time point and the sixth time point may not meet the first boundary line and the second boundary line.

A method for generating a panoramic image using an X-ray imaging apparatus according to further embodiment of the present invention includes irradiating an object with X-rays during an exposure period; generating a plurality of frames during at least a partial period of the exposure period by detecting X-rays transmitted through the object; and generating a panoramic image by overlapping the plurality of frames. Here, the panoramic image may be generated in such a manner that the plurality of frames are overlapped and arranged along a reference line, and the reference line may be configured by connecting a plurality of reference lines including a first reference line and a second reference line. At this point, the first reference line may be a line that connects central points of a first frame at a first time point and a second frame at a second time point, the second reference line may be a line that connects central points of a third frame at a third time point and a fourth frame at a fourth time point, and the first reference line and the second reference line may have different inclinations.

A storage medium in which the method for generating a panoramic image using an X-ray imaging apparatus is stored may be provided.

A method for generating a panoramic image according to further embodiment of the present invention includes receiving a plurality of frames generated by detecting X-rays transmitted through an object; and generating a panoramic image by overlapping the plurality of frames. Here, the panoramic image may be generated in such a manner that the plurality of frames are overlapped and arranged along a reference line, and the reference line may be configured by connecting a plurality of reference lines including a first reference line and a second reference line. At this point, the first reference line may be a line that connects central points of a first frame at a first time point and a second frame at a second time point, the second reference line may be a line that connects central points of a third frame at a third time point and a fourth frame at a fourth time point, and the first reference line and the second reference line may have different inclinations from each other.

A storage medium in which the method for generating a panoramic image is stored may be provided.

[System Configuration]

FIG. 1 is a block diagram illustrating a system that includes an X-ray imaging apparatus according to embodiments of the present invention, an electronic device that works with the X-ray imaging apparatus, and the like.

Referring to FIG. 1, the system according to an embodiment of the present invention may include an X-ray imaging apparatus 1000 and an electronic device 2000.

The X-ray imaging apparatus 1000 images an object to obtain image data, and then transmits the obtained image data to the electronic device 2000. The electronic device 2000 provides a panoramic image to a user using the image data.

The image data may be a plurality of frames. Alternatively, the image data may be a panoramic image that is generated by overlapping a plurality of frames.

When the image data is a plurality of frames, the electronic device 2000 may overlap the received plurality of frames to generate a panoramic image and provide the generated panoramic image to a user.

When the image data is a panoramic image, the electronic device 2000 may provide the received panoramic image to a user.

The X-ray imaging apparatus 1000 includes a controller 1100, a movement unit 1200, an X-ray generator 1300, and an X-ray detector 1400.

The controller 1100 controls operations of the movement unit 1200, the X-ray generator 1300, and the X-ray detector 1400.

The movement unit 1200 may move the X-ray generator 1300 and the X-ray detector 1400.

The X-ray generator 1300 may irradiate an object with X-rays. The X-ray detector 1400 may generate a plurality of frames by detecting X-rays transmitted through the object.

The controller 1100 may transmit the plurality of frames received from the X-ray detector 1400 to the electronic device 2000, or may generate a panoramic image by overlapping the plurality of frames and transmit the generated panoramic image to the electronic device 2000.

The electronic device 2000 may include a processor 2100, an input unit 2200, and a display unit 2300.

The processor 2100 may control the input unit 2200 and the display unit 2300.

The processor 2100 may control the X-ray imaging apparatus 1000. The processor 2100 may control the X-ray imaging apparatus 1000 by transmitting signals to the controller 1100 of the X-ray imaging apparatus 1000.

The input unit 2200 may receive a command from a user. The input unit 2200 may be a touch screen, a keyboard, or the like. The display unit 2300 may display information to the user. The information may include a panoramic image. When the input unit 2200 is a touch screen, the display unit 2300 and the input unit 2200 may be overlapped and arranged. That is, the input unit 2200 may be arranged on a front surface of the display unit 2300 and receive a command from the user.

[X-ray Imaging Apparatus]

Subsequently, an X-ray imaging apparatus according to embodiments of the present invention will be described.

Figure 2:
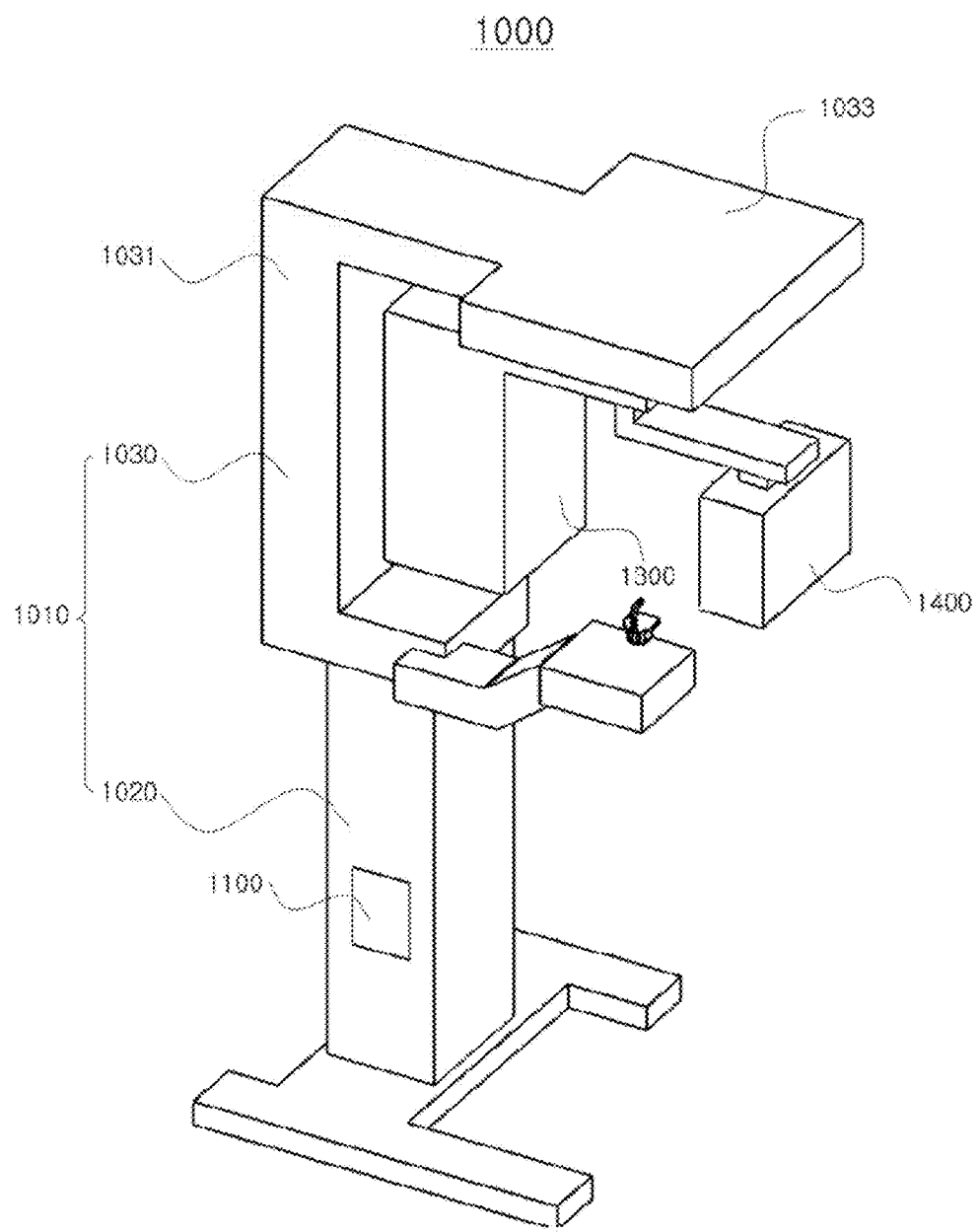
FIG. 2 is a perspective view illustrating an X-ray imaging apparatus according to an embodiment of the present invention.
Figure 3:
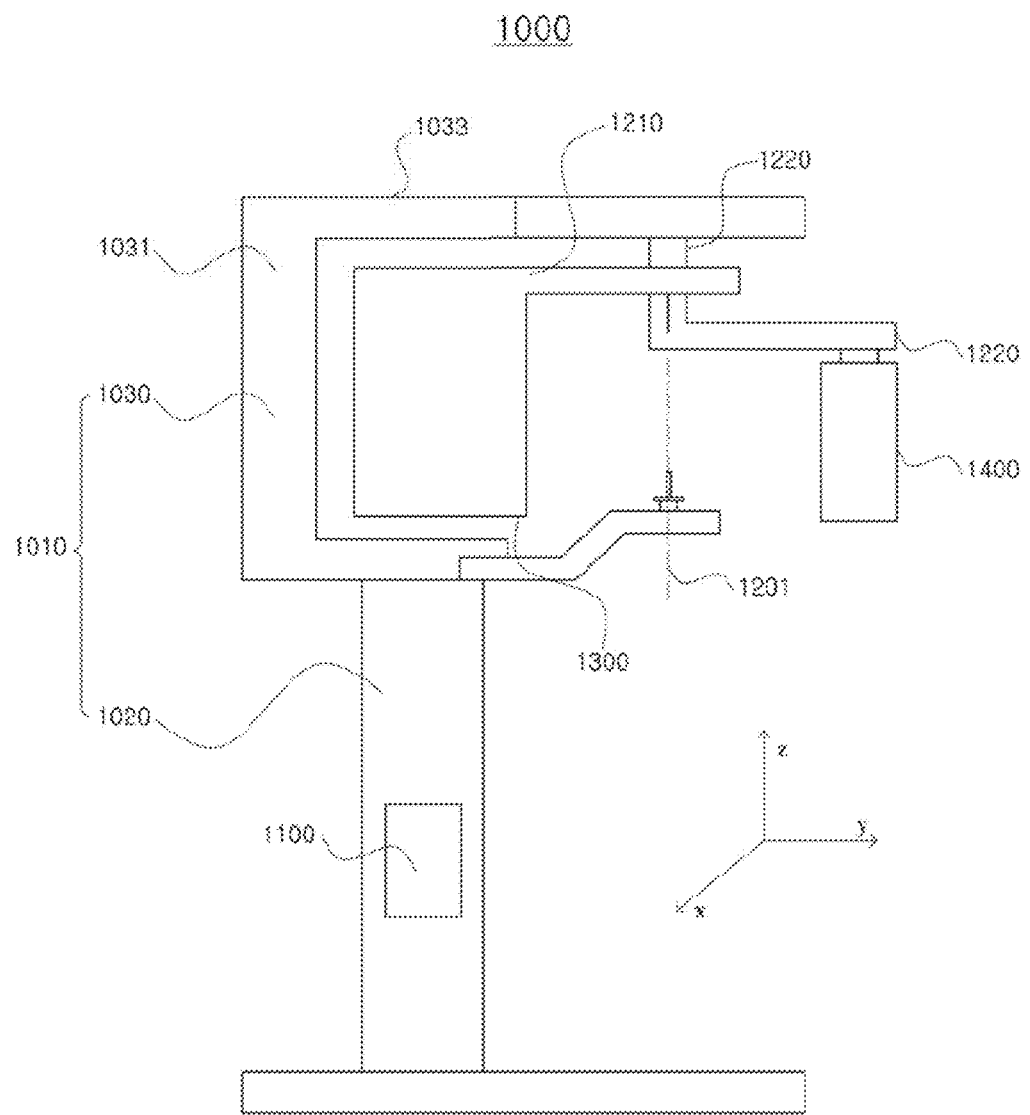
FIG. 3 is a side view illustrating an X-ray imaging apparatus according to an embodiment of the present invention.

FIG. 2 is a perspective view illustrating an X-ray imaging apparatus according to an embodiment of the present invention, and FIG. 3 is a side view illustrating an X-ray imaging apparatus according to an embodiment of the present invention.

Referring to FIGS. 2 and 3, the X-ray imaging apparatus 1000 according to an embodiment of the present invention may include the controller 1100, the movement unit 1200, the X-ray generator 1300, the X-ray detector 1400, and a body unit 1010.

The body unit 1010 may provide a frame of the X-ray imaging apparatus 1000 and have a height greater than an average height of a patient so that a teeth area of the patient which is an object may be imaged.

The controller 1100 may be located inside the body unit 1010. Alternatively, the controller 1100 may be located outside the body unit 1010.

The body unit 1010 may include a lower body 1020 and an upper body 1030. The lower body 1020 may support the upper body 1030. The lower body 1020 and the upper body 1030 may be integrally formed. The upper body 1030 may be moved in a vertical direction with respect to the lower body 1020.

The upper body 1030 may be formed to be bent. The upper body 1030 may include a vertical portion 1031 and a horizontal portion 1033. The vertical portion 1031 may have a shape that extends in the same direction as the lower body 1020. The horizontal portion 1033 may have a shape that extends in the vertical direction with respect to the vertical portion 1031. The vertical portion 1031 and the horizontal portion 1033 may be integrally formed.

The movement unit 1200 may be located below the horizontal portion 1033. The movement unit 1200 may be rotated without being fixed to the horizontal portion 1033. The movement unit 1200 may be rotated while the horizontal portion 1033 is fixed.

The movement unit 1200 may be rotated by a control of the controller 1100.

At least one of the X-ray generator 1300 and the X-ray detector 1400 may be moved by the movement unit 1200. The X-ray generator 1300 and the X-ray detector 1400 may be rotated with respect to an axis 1201 by the rotation of the movement unit 1200. The axis 1201 may be a straight line in the vertical direction from the ground. The axis 1201 may be a straight line in a z direction. A central point of the object may be positioned on the axis 1201. That is, the axis 1201 may pass through the center of the head of the patient.

The movement unit 1201 may include a first arm 1210 and a second arm 1220.

Each of the first arm 1210 and the second arm 1220 may have a shape that extends in a direction parallel to the horizontal portion 1033. The first arm 1210 and the second arm 1220 may be arranged to have an included angle. The included angle between the first arm 1210 and the second arm 1220 may be 180°. The included angle between the first arm 1210 and the second arm 1220 does not have to be 180° as long as the X-ray generator 1300 and the X-ray detector 1400 are located to have a spatial relationship required for imaging.

The first arm 1210 and the second arm 1220 may be coupled to each other to be rotated or separated from each other to be individually rotated. That is, the second arm 1220 may be simultaneously at the same time that the first arm 1210 is rotated, and an angle at which the first arm 1210 is rotated during the same time period may be the same as an angle at which the second arm 1220 is rotated. Meanwhile, the second arm 1220 may not be rotated while the first arm 1210 is rotated, and conversely, only the second arm 1220 may be rotated while the first arm 1210 is not rotated. The first arm 1210 and the second arm 1220 may be rotated with respect to the axis 1201. A rotational axis of each of the first arm 1210 and the second arm 1220 may be the same. The same rotational axis may be the axis 1201.

The first arm 1210 may be connected to the X-ray generator 1300. The X-ray generator 1300 may be moved by the movement of the first arm 1210. The first arm 1210 is rotated with respect to the axis 1201 so that the X-ray generator 1300 is also rotated with respect to the axis 1201.

The second arm 1220 may be connected to the X-ray detector 1400. The X-ray detector 1400 may be moved by the movement of the second arm 1220. The second arm 1220 is rotated with respect to the axis 1201 so that the X-ray detector 1400 is also rotated with respect to the axis 1201.

The first arm 1210 and the second arm 1220 may have an included angle of 180° so that the X-ray generator 1300 and the X-ray detector 1400 may also have an included angle of 180° with respect to the axis 1201. The X-ray generator 1300 and the X-ray detector 1400 may be rotated with respect to the axis 1201 while having the included angle of 180°. The X-ray generator 1300 and the X-ray detector 1400 may be rotated while facing each other.

The X-ray generator 1300 may be rotated along an arc. The movement of the X-ray generator 1300 which draws the arc will be described below.

[X-ray Generator]

Subsequently, a structure of the X-ray generator will be described.

Figure 4:
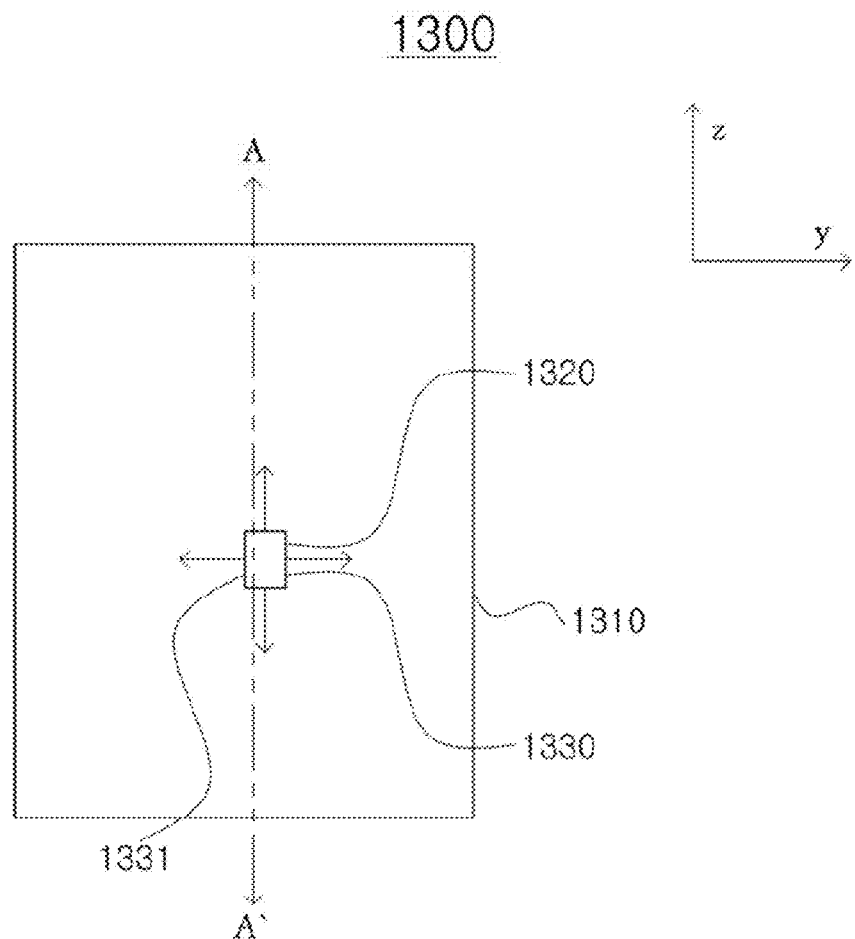
FIG. 4 is a front view illustrating an X-ray generator according to an embodiment of the present invention.
Figure 5:
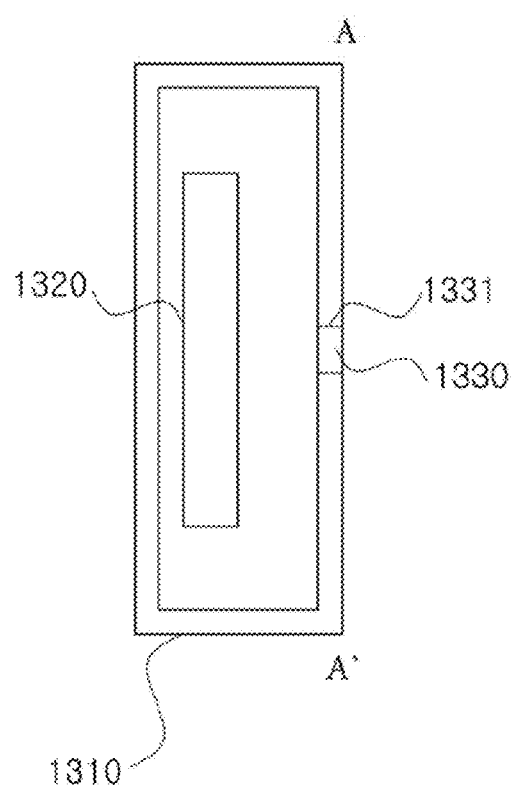
FIG. 5 is a cross-sectional view of the X-ray generator of FIG. 4 taken along line A-A'.

FIG. 4 is a front view illustrating an X-ray generator according to an embodiment of the present invention, and FIG. 5 is a cross-sectional view of the X-ray generator of FIG. 4 taken along line A-A'.

Referring to FIGS. 4 and 5, the X-ray generator 1300 according to an embodiment of the present invention may include a generator housing 1310 and an X-ray emitting unit 1320.

The X-ray emitting unit 1320 may be located inside the generator housing 1310.

The inside of the generator housing 1310 may have a rectangular box shape whose inside is empty. A rectangular box shape has been described as the shape of the generator housing 1310, but the present invention is not limited thereto. The X-ray emitting unit 1320 may be accommodated in the interior space of the generator housing 1310.

The X-ray emitting unit 1320 may emit X-rays. The X-ray emitting unit 1320 may emit X-rays in one direction or in all directions. The X-ray emitting unit 1320 may emit X-rays through a front surface of the X-ray emitting unit 1320. For example, when having a hexahedral shape, the X-ray emitting unit 1320 may emit X-rays in a normal direction of the hexahedron. The X-ray emitting unit 1320 may emit X-rays toward one surface of the generator housing 1310.

An optical path restricting unit 1330 may be located in one surface of the generator housing 1310. The one surface of the generator housing 1310 may be one surface arranged on an optical path between the X-ray emitting unit 1320 and the X-ray detector 1400. The optical path restricting unit 1330 may restrict a path of the X-rays emitted from the X-ray emitting unit 1320 and output the X-rays to the outside of the generator housing 1310. The optical path restricting unit 1330 may restrict an emission path of the X-rays so that the X-rays may be output only toward a specific area.

The optical path restricting unit 1330 may restrict X-rays with a wide area emitted from the X-ray emitting unit 1320 into X-rays with a narrow area, and output the restricted X-rays to the outside of the generator housing 1310.

The X-ray emitting unit 1320 may emit X-rays toward the one surface of the generator housing 1310 in which the optical path restricting unit 1330 is located, and the optical path restricting unit 1330 may restrict a path of the X-rays irradiated toward the one surface of the generator housing 1310 and output the restricted path of the X-rays to the outside of the generator housing 1310.

The X-ray emitting unit 1320 may emit X-ray in all directions, and the optical path restricting unit 1330 may output the X-rays, which have been reflected by an inner surface of the generator housing 1310 and have reached the optical path restricting unit 1330, to the outside of the generator housing 1310.

The optical path restricting unit 1330 may include an X-ray emission outlet 1331. The X-ray emission outlet 1331 may be a hole that passes from the outside to the inside of the generator housing 1310. An area other than the X-ray emitting outlet 1331 may be an area that does not transmit X-rays to the outside of the X-ray generator 1300. The X-ray emission outlet 1331 may provide a path through which the X-rays emitted from the X-ray emitting unit 1320 are transmitted to the outside of the generator housing 1310. The X-ray emission outlet 1331 may be a formed in a rectangular shape. The shape of the X-ray emission outlet 1331 is shown as a rectangular shape in the drawing, but is not limited thereto.

The optical path restricting unit 1330 may adjust a position or angle of the X-ray emission outlet 1331. The optical path restricting unit 1330 may adjust an emission path of X-rays transmitted to the outside of the generator housing 1310 by adjusting the position or angle of the X-ray emission outlet 1331.

The optical path restricting unit 1330 may move the position of the X-ray emission outlet 1331 in a vertical or lateral direction. The optical path restricting unit 1330 may move the X-ray emission outlet 1331 to an arbitrary position on the one surface of the generator housing 1310. When the optical path restricting unit 1330 moves the position of the X-ray emission outlet 1331 in an upward direction, X-rays output from the X-ray generator 1300 may be moved in the upward direction, and when the optical path restricting unit 1330 moves the position of the X-ray emission outlet 1331 in a downward direction, X-rays output from the X-ray generator 1300 may be moved in the downward direction.

The optical path restricting unit 1330 may adjust the angle of the X-ray emission outlet 1331 in the vertical or lateral direction. That is, a region of the X-ray emission outlet 1331 which is adjacent to the X-ray detector 1400 may be moved while a region of the X-ray emission outlet 1331 which is adjacent to the X-ray emission unit 1320 is kept fixed so that the angle of the X-ray emission outlet 1331 may be adjusted. When the X-ray emission outlet 1331 is tilted toward an upper side with respect to an XY plane, the X-ray generator 1300 may output X-rays toward a relatively upper side, and when the X-ray emission outlet 1331 is tilted toward a lower side with respect to the XY plane, the X-ray generator 1300 may output X-rays toward a relatively lower side.

In the drawing, an example in which the optical path restricting unit 1330 constitutes the one surface of the generator housing 1310 has been described, but the optical path restricting unit 1330 may be positioned in such a manner as to be installed on the one surface of the generator housing 1310. When the optical path restricting unit 1330 is positioned in such a manner as to be attached to the one surface of the generator housing 1310, an emission outlet with a larger size than that of the X-ray emission outlet 1331 may be formed on the one surface of the generator housing 1310 in which the optical path restricting unit 1330 is positioned, and the X-ray emission outlet 1331 may be moved within an area of the emission outlet to restrict an output path of the X-rays.

The X-ray generator 1300 may move the output path of the X-rays in a Z-axis direction through the optical path restricting unit 1330. The X-ray generator 1300 may move the output path of the X-rays so that it corresponds to a location of the X-ray detector 1400.

Alternatively, although not shown, in a state in which the optical path restricting unit 1330 outputs X-rays in a predetermined path, the entire X-ray generator 1300 may be moved to move the output path of the X-rays through the optical path restricting unit 1330. That is, instead of a method of selectively moving only the optical path restricting unit 1330, the entire X-ray generator 1300 may be moved to move the output path of the X-rays so that the output path of the X-rays may correspond to the location of the X-ray detector 1400. In other words, the generator housing 1310 may be moved to move the output path of the X-rays. In this case, the X-ray generator 1300 according to an embodiment of the present invention may further include a linear movement unit that separately moves the generator housing 1310.

[X-ray Detector]

Subsequently, a structure of the X-ray detector will be described.

Figure 6:
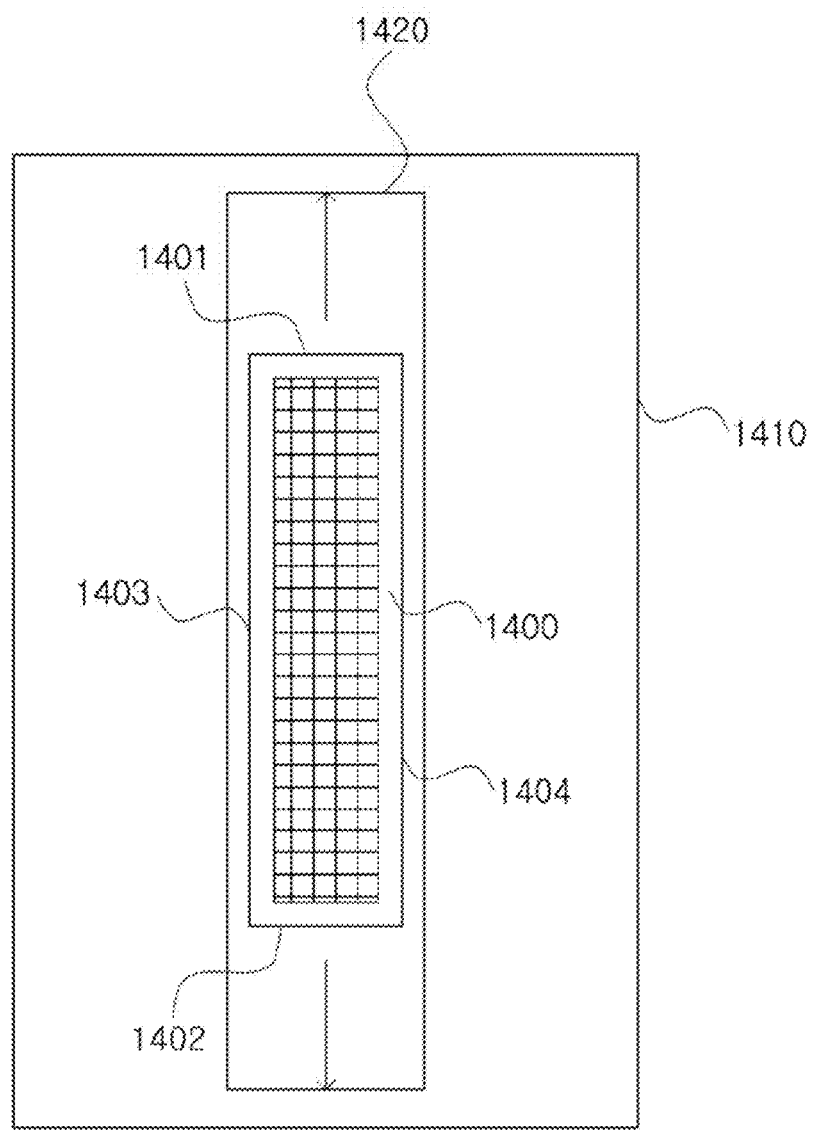
FIG. 6 is a front view illustrating an X-ray detector according to an embodiment of the present invention.
Figure 7:
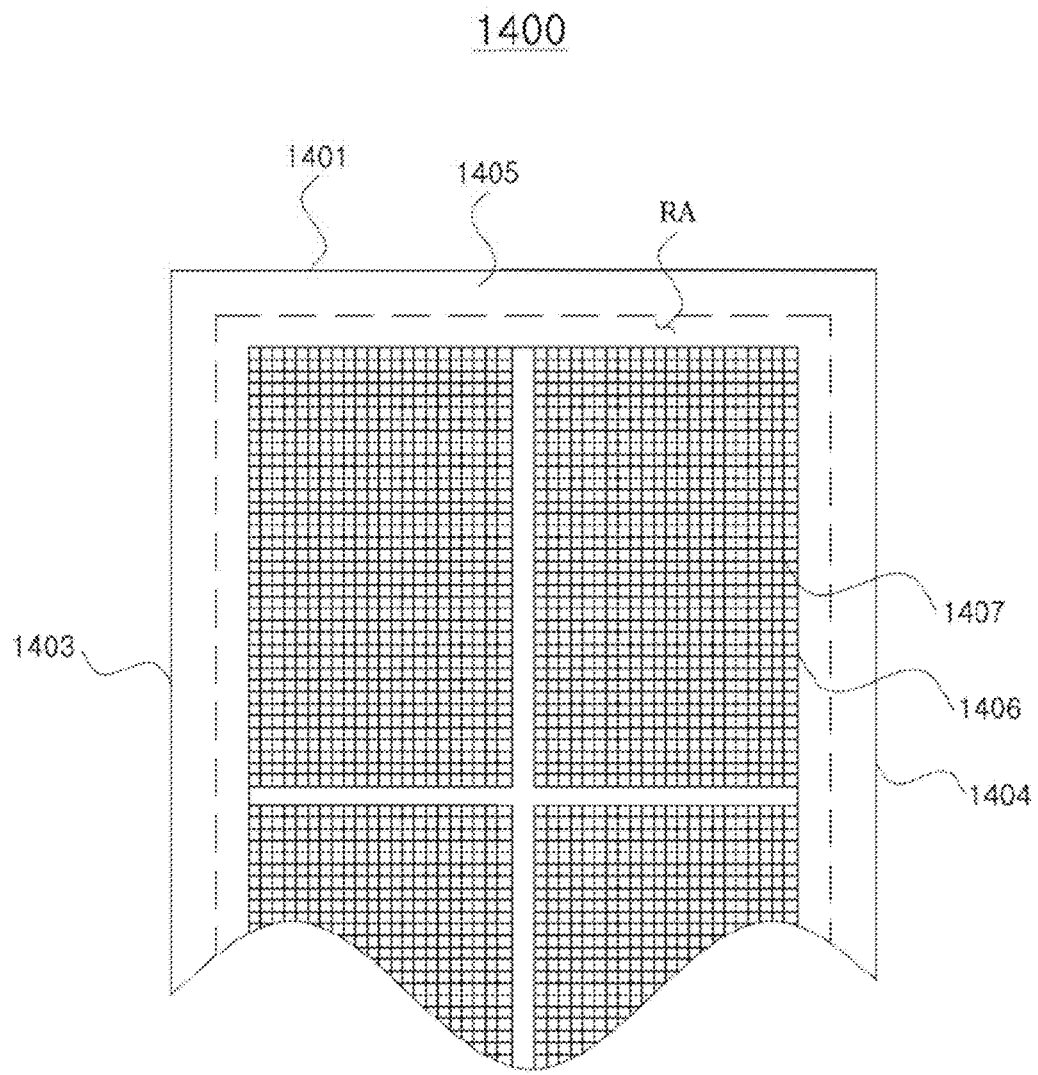
FIG. 7 is an enlarged view illustrating a part of an image sensor according to an embodiment of the present invention.

FIG. 6 is a front view illustrating an X-ray detector according to an embodiment of the present invention, and FIG. 7 is an enlarged view illustrating a part of an image sensor according to an embodiment of the present invention.

Referring to FIGS. 6 and 7, the X-ray detector 1400 according to an embodiment of the present invention may be located in a detector housing 1410.

The X-ray detector 1400 may be installed in the detector housing 1410. The X-ray detector 1400 may be installed in one surface of the detector housing 1410.

The detector housing 1410 may include a sensor movement region 1420. The sensor movement region 1420 may be positioned on one surface of the detector housing 1410. The sensor movement region 1420 may be a region that opens a partial region of the one surface of the detector housing 1410. The sensor movement region 1420 may provide a movement path of the X-ray detector 1400.

The sensor movement region 1420 may be formed to have an area larger than that of the X-ray detector 1400. The sensor movement region 1420 may be formed in such a manner as to extend in a longitudinal direction of the X-ray detector 1400.

The X-ray detector 1400 may be formed in a rectangular shape. The X-ray detector 1400 may be formed in a rectangular shape such that a first boundary surface 1401 and a second boundary surface 1402 face each other and a third boundary surface 1403 and a fourth boundary surface 1404 face each other. The first boundary surface 1401 may have the same length as the second boundary surface 1402, and the third boundary surface 1403 may have the same length as the fourth boundary surface 1403. The first boundary surface 1401 may have a length shorter than that of the third boundary surface 1403.

The X-ray detector 1400 may also have a square shape. The X-ray detector 1400 may be used for CT.

The sensor movement region 1420 may be formed in such a manner as to extend in a direction parallel to the third boundary surface 1403. The sensor movement region 1420 may provide a space in which the X-ray detector 1400 is moveable in the direction parallel to the third boundary surface 1403.

The X-ray detector 1400 may be moved in a linear direction within the sensor movement region 1420. That is, the X-ray detector 1400 may be moved in the linear direction parallel to the third boundary surface 1403 within an open region of the sensor movement region 1420.

The movement of the X-ray detector 1400 in a direction of the second boundary surface 1402 may be defined as a first linear motion, and the movement of the X-ray detector 1400 in a direction of the first boundary surface 1401 may be defined as a second linear motion. The X-ray detector 1400 may be moved a reciprocating motion sequentially including the first linear motion and the second linear motion by a control of the controller 1100.

For example, the X-ray detector 1400 may be initially located at a first position, reach a second position through the first linear motion, and then reach the first position through the second linear motion. The first position may be a position that is close to a boundary portion of the sensor movement region 1420 adjacent to the first boundary surface 1401, and the second position may be a position that is close to the sensor movement region 1420 adjacent to the second boundary surface 1402.

That is, by the first linear motion, the open region of the sensor movement region 1420 which has the first boundary surface 1401 as one side may be increased while at the same time decreasing the open region of the sensor movement region 1420 which has the second boundary surface 1402 as one side. In addition, by the second linear motion, the open region of the sensor movement region 1420 which has the first boundary surface 1401 as one side may be decreased while at the same time increasing the open region of the sensor movement region 1420 which has the second boundary surface 1402 as one side.

The X-ray detector 1400 may be moved along a structure such as a rail or the like within the sensor movement region 1420. A rail has been described as the movement structure of the X-ray detector 1400, but the present invention is not limited thereto.

The X-ray detector 1400 may include a detector body 1405 and a plurality of image sensor tiles 1406 which are formed in the detector body 1405. The plurality of image sensor tiles 1406 may be arranged on the detector body 1405.

Each of the plurality of image sensor tiles 1406 may have a constant interval between adjacent tiles. Alternatively, each of the plurality of image sensor tiles 1406 may be located in contact with adjacent tiles. Each of the plurality of image sensor tiles 1406 may have a plurality of pixels. The plurality of pixels may be arranged in a matrix form.

A light receiving area RA may be defined on the X-ray detector 1400. The light receiving area RA may be an area irradiated with X-rays from the X-ray detector 1300. The light receiving area RA may be an area that includes the image sensor tiles 1406. The light receiving area RA may be an area that includes all of the image sensor tiles 1406. The X-ray generator 1300 may be controlled such that a boundary portion of the light receiving area RA may be located between the image sensor tiles 1406 and the first to fourth boundary surfaces 1401 to 1404. By controlling the optical path restricting unit 1330 of the X-ray generator 1300 so that the boundary portion of the light receiving area RA is located between the image sensor tiles 1406 and the first to fourth boundary surfaces 1401 to 1404, it is possible to prevent the X-rays from being irradiated to the outside of the detector body 1405, thereby preventing the X-ray exposure. In addition, by controlling the optical path restricting unit 1330 so that the light receiving area RA includes all of the image sensor tiles 1406, it is possible to use all of the image sensor tiles 1406 to detect X-rays.

[Rotation of X-ray Generator and X-ray Detector]

Subsequently, a rotating operation of the X-ray generator and the X-ray detector will be described.

Figure 8:
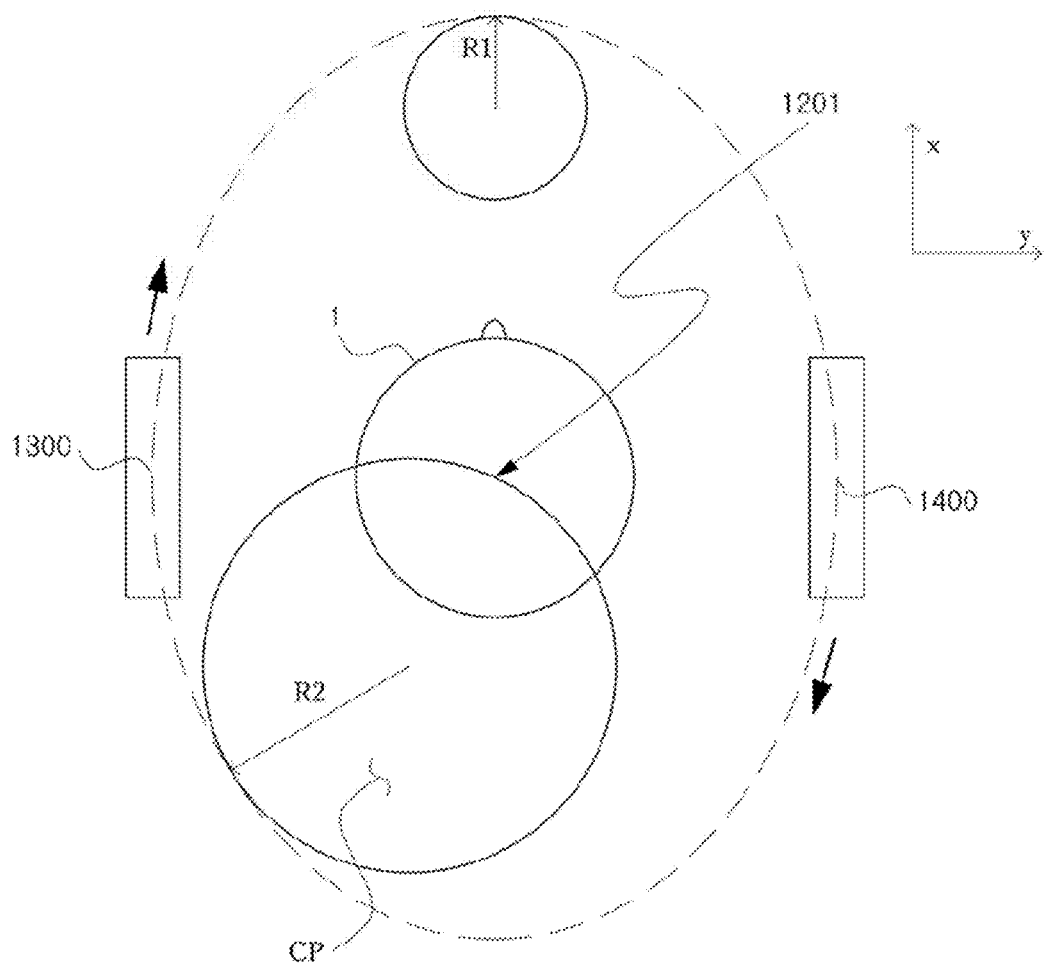
FIG. 8 is a top view illustrating rotation of each of an X-ray generator and an X-ray detector according to an embodiment of the present invention.

FIG. 8 is a top view illustrating rotation of each of an X-ray generator and an X-ray detector according to an embodiment of the present invention.

Referring to FIG. 8, when the X-ray imaging apparatus according to an embodiment of the present invention is viewed from the Z-axis direction, an object 1 may be disposed such that a center of the object 1 may be located on the axis 1201. That is, a patient may be placed such that the axis 1201 may be located at the center of the head of the patient.

The X-ray generator 1300 and the X-ray detector 1400 may be rotated while facing each other. The X-ray generator 1300 and the X-ray detector 1400 may be moved in a clockwise direction with respect to the axis 1201. In the drawing, an example in which the X-ray generator 1300 and the X-ray detector 1400 are moved in the clockwise direction has been described, but the X-ray generator 1300 and the X-ray detector 1400 may be moved in a counterclockwise direction.

When viewed from the top, the X-ray generator 1300 and the X-ray detector 1400 may be moved along a movement path. The movement path may be a predetermined path. The movement path may be preset by a user. The movement path may be predetermined. In addition, the movement path may be set by detecting characteristics of the object.

The X-ray generator 1300 may be moved along a curve shaped-movement path. The X-ray generator 1300 may be moved along an elliptically shaped-movement path.

The X-ray generator 1300 may be moved along an arc. The X-ray generator 1300 may be moved while drawing the arc having a radius of curvature within a range. That is, the movement path of the X-ray generator 1300 may be the arc having a radius of curvature within the range. The movement path of the X-ray generator 1300 may be an arc having a radius of curvature in a range of a first radius R1 to a second radius R2. The X-ray generator 1300 may be moved while drawing an arc having a predetermined radius of curvature. At this point, the movement path of the X-ray generator 1300 may be a circle. When the movement path of the X-ray generator 1300 is a circle, a distance between the axis 1201 and the X-ray generator 1300 may be the same as the radius of curvature.

Alternatively, the X-ray generator 1300 may be moved along an arc having a radius of curvature which is changed. The radius of curvature of the X-ray generator 1300 may be changed within the range of the first radius R1 to the second radius R2. A ratio of the first radius R1 and the second radius R2 may be 1:1.01 to 1:100.

When the X-ray generator 1300 has an arc having a radius of curvature which is changed, a plurality of circles may all be located on the same plane CP.

Although not shown, the X-ray generator 1300 may perform a motion to draw an ellipse. When the X-ray generator 1300 performs the motion to draw an ellipse, the axis 1201 may be moved in a direction of a major axis of the ellipse. In this case, the X-ray generator 1300 may perform a linear motion in a partial interval. Alternatively, the X-ray generator 1300 may perform a motion which converges to the linear motion.

[Linear Motion of X-ray Detector]

Subsequently, the linear motion of the X-ray detector will be described.

Figure 9:
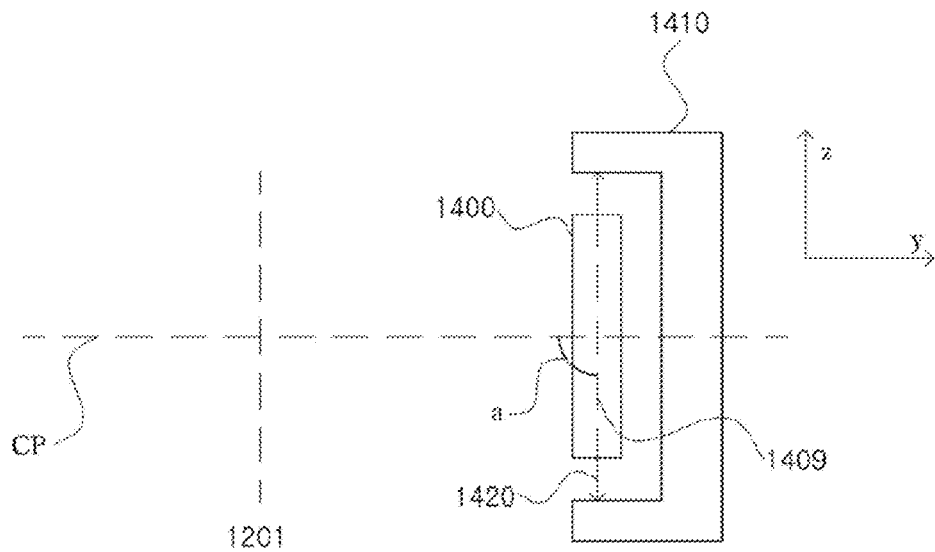
FIG. 9 is a view illustrating a linear motion of an X-ray detector according to an embodiment of the present invention.

FIG. 9 is a view illustrating a linear motion of an X-ray detector according to an embodiment of the present invention.

Referring to FIG. 9, the X-ray detector 1400 according to an embodiment of the present invention may be located in the detector housing 1410.

The X-ray detector 1400 may be moved in a linear direction. The X-ray detector 1400 may perform a linear motion. As described above, the X-ray generator 1300 may be moved while drawing an arc having a radius of curvature within the range. A plurality of circles having a radius of curvature within the range may be respectively located on a two-dimensional (2D) plane. The plurality of circles having a radius of curvature within the range may be located on the same 2D plane. In the drawing, an example in which the circles are located on an XY plane has been described, but the plurality of circles may be located on a plane other than the XY plane.

The X-ray detector 1400 may perform a linear motion in a linear direction having an angle a with respect to the plane CP where at least one circle of the plurality of circles having a radius of curvature within the range is located. The X-ray detector 1400 may perform a linear motion along a linear movement axis 1409. The plane CP where the linear movement axis 1409 of the X-ray detector 1400 and the circle is located may have the angle a.

The plurality of circles may all be located on the same plane, and in this case, the X-ray detector 1400 may perform a linear motion in the linear direction having the angle a with respect to the plane where the plurality of circles having a radius of curvature within the range are located.

The angle a formed by the plane CP where the circle is located and the linear movement axis 1409 of the X-ray detector 1400 may be 60 to 120°. Preferably, the angle a may be 80 to 100°. More preferably, the angle a may be 90°.

The angle a may be determined according to a position of the plane CP where the circle is located. The angle a may be determined according to a position on a Z-axis of the plane CP where the circle is located. The angle a may be determined according to a distance by which the plane CP where the circle is located is spaced apart from a central point of the Z direction of the X-ray detector 1400 before the linear motion. When the distance between the plane CP where the circle is located and the central point of the Z direction of the X-ray detector 1400 before the linear motion is large, the angle a may be far from 90°. That is, in this case, the angle a may be decreased. When the distance between the plane CP where the circle is located and the central point of the Z direction of the X-ray detector 1400 before the linear motion is small, the angle a may be close to 90°. That is, in this case, the angle a may be increased.

The linear movement axis 1409 may be parallel to the axis 1201.

The linear movement axis 1409 may be set to be perpendicular to an angle at which X-rays are irradiated from the X-ray generator 1300.

The linear movement axis 1409 may be parallel to at least a partial region of an X-ray light receiving surface of the X-ray detector 1400. The X-ray light receiving surface may be a surface irradiated with the X-rays from the X-ray generator 1300.

The X-ray detector 1400 may perform a linear motion along the linear movement axis 1409 parallel to the X-ray light receiving surface, and therefore may perform a linear motion in a direction perpendicular to the X-rays irradiated from the X-ray generator 1300. That is, the X-ray detector 1400 may be moved in a linear direction in a state in which the at least a partial region of the X-ray detector 1400 is maintained to be perpendicular to the X-rays irradiated from the X-ray generator 1300.

The linear movement axis 1409 may be set to be parallel to at least the partial region of the X-ray light receiving surface of the X-ray detector 1400 so that at least the partial region of the X-ray detector 1400 may be irradiated with the X-rays in a vertical direction, thereby reducing energy loss in an X-ray irradiation process. As a result, an image quality of a frame generated by the X-ray detector 1400 may be improved.

[Operation of X-ray Imaging Apparatus in Embodiment]

—Operational Method of X-ray Imaging Apparatus—

Figure 10:
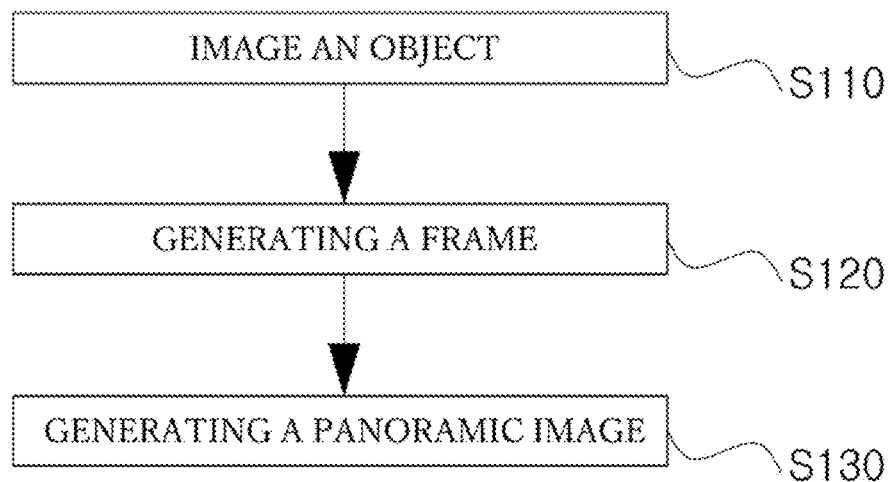
FIG. 10 is a flowchart illustrating a method for operating an X-ray imaging apparatus according to an embodiment of the present invention.

FIG. 10 is a flowchart illustrating a method for operating an X-ray imaging apparatus according to an embodiment of the present invention.

Referring to FIG. 10, the method for operating the X-ray imaging apparatus 1000 according to an embodiment of the present invention includes imaging an object (S110), generating a frame (S120), and generating a panoramic image (S130).

Detailed description of each operation is as follows.

—Imaging of Object—

Figure 11:
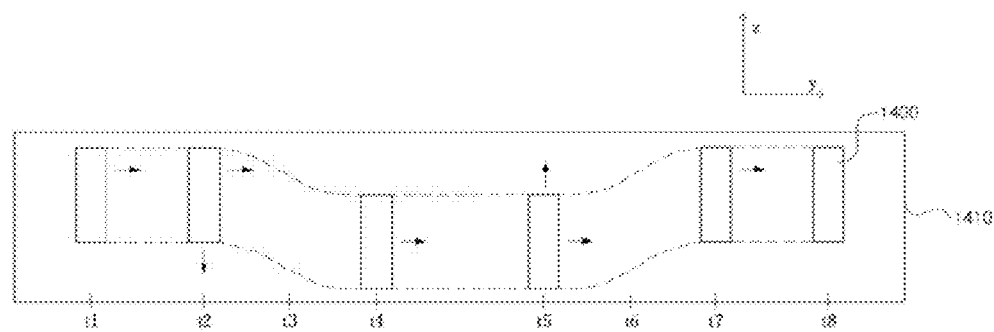
FIG. 11 is a view illustrating a movement path of an X-ray detector according to an embodiment of the present invention.

FIG. 11 is a view illustrating a movement path of an X-ray detector according to an embodiment of the present invention.

Referring to FIG. 11, the X-ray detector 1400 according to an embodiment of the present invention may be moved on the detector housing 1410.

In the drawing, the X-ray detector 1400 and the detector housing 1410 are shown to be formed integrally, but the movement of the detector housing 1410 is shown successively over time. In addition, in the drawing, six X-ray detectors 1400 are shown, but positions at a specific time point of the X-ray detector 1400 that is moved successively is shown.

The X-ray detector 1400 starts to be moved at a first time point t1 and ends its movement at an eighth time point t8. The X-ray detector 1400 may be moved along a movement path during the first time point t1 to the eighth time point t8. The X-ray detector 1400 may be moved along the movement path by a control of the controller 1100.

The X-ray generator 1300 may emit X-rays during a movement time of the X-ray detector 1400. During an exposure period during which the X-ray generator 1300 emits X-rays, the X-ray generator 1300 may be moved along the movement path.

The X-ray generator 1300 may be moved along the movement path.

The exposure period may be the same as the movement time of the X-ray detector 1400. That is, the exposure period may start at the first time point t1 and end at the eighth time point t8. In other words, the X-ray generator 1300 may emit light at the same time the X-ray detector 1400 starts to be moved, and the X-ray generator 1300 may stop emitting light at the same time the movement of the X-ray detector 1400 ends.

The exposure period may include the movement time of the X-ray detector 1400. That is, the exposure period may start before the first time point t1 and end after the eighth time point t8. In other words, the X-ray detector 1400 may start to be moved after the X-ray generator 1300 starts emitting light, and the X-ray generator 1300 may stop emitting light after the movement of the X-ray detector 1400 ends.

The exposure period may be included in the movement time of the X-ray detector 1400. That is, the exposure period may start at a time point later than the first time point t1 and end before the eighth time point t8. In other words, the X-ray generator 1300 may emit light after the X-ray detector 1400 starts being moved, and the movement of the X-ray detector 1400 may be ended after the X-ray generator 1300 stops emitting light.

The exposure period may start earlier than the first time point t1 and end earlier than the eighth time point t8. In addition, the exposure period may start later than the first time point t1 and end earlier than the eighth time point t8.

The movement of the X-ray detector 1400 will be described again. The X-ray detector 1400 may perform a linear motion during a period of a second time point t2 to a seventh time point t7 while maintaining a motion along an arc. A difference between the first time point t1 and the eighth time point t8 during which the X-ray detector 1400 is moved along the arc may be larger than a difference between the second time point t2 and the seventh time point t7 during which the X-ray detector 1400 is moved in a linear direction.

Alternatively, a first difference may be the same as a second difference. When the first difference is the same as the second difference, the X-ray detector 1400 may start the motion along the arc and start the linear motion at the same time. In addition, the motion along the arc may be ended and, at the same time, the linear motion may be ended.

The motion along the arc performed by the X-ray detector 1400 may have a speed. Alternatively, the motion along the arc performed by the X-ray detector 1400 may have a different speed for each interval.

The X-ray detector 1400 may start to be moved at the first time point t1. During the first time point t1 to the second time point t2, the X-ray detector 1400 may be moved along an arc with respect to the axis 1201 of FIG. 3. That is, the X-ray detector 1400 may be moved to an XY plane in a state in which a constant position of the X-ray detector 1400 is maintained with respect to the Z-axis direction. That is, the X-ray detector 1400 may be moved in a direction parallel to the ground between the first time point t1 and the second time point t2. The X-ray detector 1400 may be located at a first position within the detector housing 1401 between the first time point t1 and the second time point t2.

The X-ray detector 1400 may start a first linear motion while maintaining the motion along the arc at the second time point t2. The first linear motion may be a movement in the Z-axis direction. The first linear motion may be a movement in the Z-axis direction that is oriented toward the ground. The X-ray detector 1400 may be lowered in a direction of the ground by the first linear motion. The linear motion of the X-ray detector 1400 may start at the second time point t2 and end at a fourth time point t4. The X-ray detector 1400 may be moved along a curved movement path due to a combination of the motion along the arc and the first linear motion. The X-ray detector 1400 may be moved along the curved movement path when viewed from the outside by the motion along the arc caused by the movement unit 1200 and the linear motion of the X-ray detector 1400 within the detector housing 1410. The X-ray detector 1400 may be located at the first position within the detector housing 1410 at the second time point t2, and may be located at a second position within the detector housing 1410 at the fourth time point t4 by the first linear motion.

During the second time point t2 to the fourth time point t4, the X-ray detector 1400 may perform the first linear motion at the same speed. When performing the first linear motion at the same speed during the second time point t2 to the fourth time point t4, the X-ray detector 1400 may be moved along a linear movement path in a diagonal direction when viewed from the outside.

Alternatively, the X-ray detector 1400 may be moved while the speed of the first linear motion is changed during the second time point t2 to the fourth time point t4.

For example, at a third time point t3 between the second time point t2 and the fourth time point t4, a change amount of the speed of the first linear motion may be changed. The speed of the first linear motion may be gradually increased between the second time point t2 and the third time point t3. Due to the gradual increase in the speed of the first linear motion between the second time point t2 and the third time point t3, the X-ray detector 1400 may be moved along a movement path that draws a curve in which an absolute value of inclination increases from the second time point t2 to the third time point t3.

The speed of the first linear motion may be gradually reduced between the third time point t3 and the fourth time point t4. Due to the gradual reduction in the speed of the first linear motion between the third time point t3 and the fourth time point t4, the X-ray detector 1400 may be moved along a movement path that draws a curve in which the absolute value of the inclination decrease from the third time point t3 to the fourth time point t4.

The X-ray detector 1400 may end the first linear motion at the fourth time point t4 and perform only the motion along the arc with respect to the axis 1201 between the fourth time point t4 and a fifth time point t5. That is, the X-ray detector 1400 may be moved to the XY plane while maintaining a constant position with respect to the Z-axis direction. That is, the X-ray detector 1400 may be moved in a direction parallel to the ground between the fourth time point t4 and the fifth time point t5. The X-ray detector 1400 may be located at the second position within the detector housing 1410 between the fourth time point t4 and the fifth time point t5.

The X-ray detector 1400 may start a second linear motion while maintaining the motion along the arc at the fifth time point t5. The second linear motion may be a movement in the Z-axis direction. The second linear motion may be a movement in the Z-axis direction opposite to the ground. The X-ray detector 1400 may be raised in a direction away from the ground by the second linear motion. The linear motion of the X-ray detector 1400 may start at the fifth time point t5 and end at the seventh time point t7. The X-ray detector 1400 may be moved along a curved movement path due to a combination of the motion along the arc and the second linear motion. The X-ray detector 1400 may be moved along the curved movement path when viewed from the outside, by the motion along the are caused by the movement unit 1200 and the linear motion of the X-ray detector 1400 within the detector housing 1410. The X-ray detector 1400 may be located at the second position within the detector housing 1410 at the fifth time point t5, and may be located at the first position within the detector housing 1410 at the seventh time point t7 by the second linear motion.

The first linear motion and the second linear motion may constitute the linear motion of the X-ray detector 1400. That is, the linear motion may be a linear reciprocating motion.

During the fifth time point t5 to the seventh time point t7, the X-ray detector 1400 may perform the second linear motion at the same speed. When performing the second linear motion at the same speed during the fifth time point t5 to the seventh time point t7, the X-ray detector 1400 may be moved along a linear movement path in a diagonal direction when viewed from the outside.

Alternatively, the X-ray detector 1400 may be moved while the speed of the second linear motion is changed during the fifth time point t5 to the seventh time point t7.

For example, at a sixth time point t6 between the fifth time point t5 and the seventh time point t7, a change amount of the speed of the second linear motion may be changed. The speed of the second linear motion may be gradually increased between the fifth time point t5 and the sixth time point t6. Due to the gradual increase in the speed of the second linear motion between the fifth time point t5 and the sixth time point t6, the X-ray detector 1400 may be moved along a movement path that draws a curve in which the absolute value of the inclination increases from the sixth time point t6 to the fifth time point t5.

The speed of the second linear motion may be gradually reduced between the sixth time point t6 and the seventh time point t7. Due to the gradual reduction in the speed of the second linear motion between the sixth time point t6 and the seventh time point t7, the X-ray detector 1400 may be moved along a movement path that draws a curve in which the absolute value of the inclination decreases from the seventh time point t7 to the sixth time point t6.

The X-ray detector 1400 may end the second linear motion at the seventh time point t7 and perform only the motion along the arc with respect to the axis 1201 between the seventh time point t7 and the eighth time point t8. That is, the X-ray detector 1400 may be moved to the XY plane while maintaining a constant position with respect to the Z-axis direction. That is, the X-ray detector 1400 may be moved in a direction parallel to the ground between the seventh time point t7 and the eighth time point t8. The X-ray detector 1400 may be located at the first position within the detector housing 1410 between the seventh time point t7 and the eighth time point t8. When the eighth time point t8 is reached, the X-ray detector 1400 stops being moved.

The movement path of the X-ray detector 1400 may be predefined. Alternatively, the movement path of the X-ray detector 1400 may be determined depending on the shape of the object. That is, the movement path of the X-ray detector 1400 may be determined by sensing the shape of the object.

The X-ray generator 1300 may move the output path of the X-ray so that it corresponds to the movement of the X-ray detector 1400. The X-ray generator 1300 may move the output path of the X-ray by controlling the optical path restricting unit 1330 as shown in FIGS. 4 and 5. Alternatively, although not shown, in a state in which the optical path restricting unit 1330 outputs X-rays to a constant path, the entire X-ray generator 1300 may be moved to move the output path of the X-ray.

The X-ray generator 1300 and the X-ray detector 1400 may perform the motion along the are while maintaining a state in which they face each other by the movement unit 1200, and since the X-ray detector 1400 may perform the linear motion during the motion to draw the arc, only the linear motion may be detected when the X-ray detector 1400 is viewed from the point of view of the X-ray generator 1300. That is, the X-ray detector 1400 may perform the linear motion with respect to the X-ray generator 1300. In other words, the X-ray detector 1400 may appear to perform the first linear motion between the second time point t2 and the fourth time point t4 and the second linear motion between the fifth time point t5 and the seventh time point t7 with respect to the X-ray generator 1300. The X-ray detector 1400 may perform a relative position movement in the Z-axis direction with respect to the X-ray generator 1300.

Accordingly, since the X-ray generator 1300 may also move the output path of the X-ray in the Z-axis direction, it may adjust the output path of the X-ray so that it corresponds to the movement of the X-ray detector 1400.

—Generation of Frame—

Figure 12:
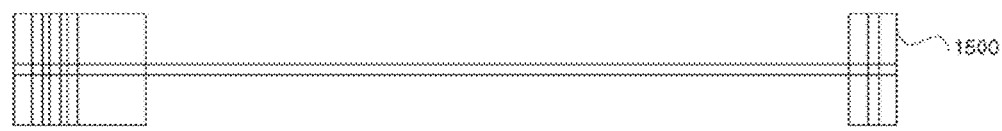
FIG. 12 is a view illustrating a plurality of frames generated according to an embodiment of the present invention.

FIG. 12 is a view illustrating a plurality of frames generated according to an embodiment of the present invention.

Referring to FIG. 12, the X-ray detector 1400 according to an embodiment of the present invention generates a plurality of frames during an exposure period. In the drawing, a plurality of frames generated when an object is imaged corresponding to a movement path of the X-ray detector 1400 will be described.

The X-ray detector 1400 generates frames 1500 at a speed of 15 fps to 500 fps.

Each of the frames 500 may be generated by detecting X-rays irradiated from the X-ray detector 1400 at each time point. Each of the frames may be generated to have a region overlapping an adjacent frame.

The generation speed of the frames 1500 may be proportional to a movement speed of the X-ray detector 1400. When the movement speed of the X-ray detector 1400 is fast, the X-ray detector 1400 may generate the frames 1500 at a relatively high speed, and when the movement speed of the X-ray detector 1400 is slow, the X-ray detector 1400 may generate the frames 1500 at a relatively low speed.

The generation speed of the frames 1500 may be proportional to the movement speed of the X-ray detector 1400, and therefore the number of the frames 1500 generated during the exposure period may be fixed regardless of the movement speed of the X-ray detector 1400. The overlapped region of the adjacent frames 1500 may also be fixed regardless of the movement speed of the X-ray detector 1400.

The generation speed of the frames 1500 may not be dependent on the movement speed of the X-ray detector 1400. However, the generation speed of the frames 1500 should be set such that the frames 150 have the overlapped region.

In addition, an area of the overlapped region of adjacent frames 1500 may vary. That is, the X-ray detector 1400 may be moved in such a manner that the overlapped region of adjacent frames 1500 is not fixed. For example, when X-rays transmitted through a central region of the object are detected, the plurality of frames 1500 generated by the X-ray detector 1400 may have an overlapped region with a relatively wide area. In addition, an area of the overlapped region of the plurality of frames 1500 generated by the X-ray detector 1400 may be reduced as the X-ray detector 1400 moves away from the central region of the object. A resolution of the frames 150 may correspond to a resolution of the X-ray detector 1400. The resolution of the frames 1500 may be the same as the resolution of the X-ray detector 1400. The frames 1500 may have a shape corresponding to the shape of the X-ray detector 1400. Since the X-ray detector 1400 has a rectangular shape, the frames 1500 may also have a rectangular shape.

In the drawing, since the object is shaped the same as the movement path of the X-ray detector 1400, each of the frames 1500 may have a linear stripe shape in their central region. That is, a stripe shape having the same height may be detected from the point of view of the X-ray detector 1400, and therefore the plurality of frames 1500 having the linear stripe shape in their central region may be generated.

—Generation of Panoramic Image—

Figure 13:
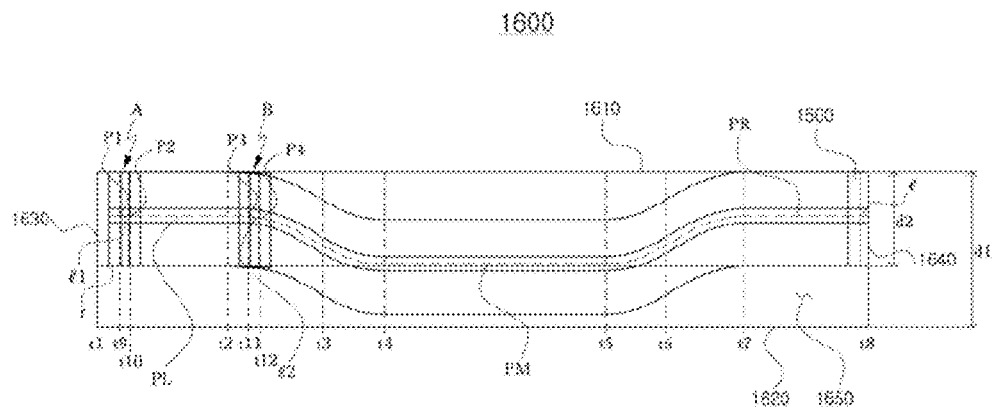
FIG. 13 is a view illustrating a panoramic image generated by an X-ray imaging apparatus according to an embodiment of the present invention.

FIG. 13 is a view illustrating a panoramic image generated by an X-ray imaging apparatus according to an embodiment of the present invention.

Referring to FIG. 13, the X-ray imaging apparatus 1000 according to an embodiment of the present invention generates a panoramic image 1600 using the plurality of frames 1500 generated by the X-ray detector 1400. The panoramic image 1600 may be generated by the controller 1100 of the X-ray imaging apparatus 1000. Alternatively, the electronic device 2000 may receive the plurality of frames 1500 generated by the X-ray detector 1400, and generate the panoramic image 1600 by the processor 2100 of the electronic device 2000. Hereinafter, an example in which the panoramic image 1600 is generated by the controller 1100 of the X-ray imaging apparatus 1000 will be described.

The controller 1100 may generate the panoramic image 1600 by overlapping the plurality of frames 1500.

The panoramic image 1600 may have a rectangular shape. The panoramic image 1600 may be a rectangular image that is defined by a first boundary line 1610, a second boundary line 1620, a third boundary line 1630, and a fourth boundary line 1640. The first boundary line 1610 and the second boundary line 1620 may be straight lines facing each other, and the third boundary line 1630 and the fourth boundary line 1640 may be straight lines facing each other.

The panoramic image 1600 may have a first width d1. The first width d1 may be a length corresponding to a length of the third boundary line 1630. The first width d1 may be a length corresponding to a length of the fourth boundary line 1640. The frames 1500 may have a second width d2. The second width d2 may be a width of the frames 1500 parallel to the third boundary line 1630 of the panoramic image 1600. The second width d2 may have a smaller value than the first width d1. That is, the first width d1 of the panoramic image 1600 may be larger than the second width d2 of the frames 1500.

The panoramic image 1600 may include a dummy region 1650. The dummy region 1650 may be a region in which the plurality of frames 1500 are not arranged. Since the second width d2 of the frames 1500 is smaller than the first width d1 of the panoramic image 1600, the frames 1500 may not be arranged in a partial region of the panoramic image 1600. Accordingly, an image that is imaged may not be displayed in the dummy region 1650. An image with a uniform gradation may be displayed in the dummy region 1650. A black image may be displayed in the dummy region 1650. Alternatively, a white image may be displayed in the dummy region 1650.

The controller 1100 may overlap the plurality of frames 1500 along a reference line l. The reference line l may be a reference for overlapping the plurality of frames 1500 generated between the first time point t1 to the eighth time point t8 which have been described in FIG. 11. The reference line may be a reference for overlapping at least one frame generated between specific time points.

The reference line l may have a shape corresponding to the movement path of the X-ray detector 1400. By overlapping the plurality of frames 1500 with respect to the reference line l having the shape corresponding to the movement path of the X-ray detector 1400, the panoramic image 1600 may be generated to have a restored shape of an object imaged by the X-ray detector 1400 while the X-ray detector 1400 is moved. The reference line l may be a virtual line. The reference line l may be a line that is predefined. The reference line l may be a line that is predefined along the movement path of the X-ray detector 1400. Alternatively, the reference line l may be a line that is determined depending on the shape of the object. That is, the reference line l may be determined by sensing the shape of the object.

The reference line 1 may include a left reference line region PL and a right reference line region PR with respect to a middle region PM of the panoramic image 1600. The left reference line region PL may have a shape that is symmetrical with the right reference line region PR.

The reference line 1 may include a plurality of reference line regions. A reference line region may be a region obtained by dividing the reference line according to intervals.

A reference line region between the first time point t1 and the second time point t2 may be a straight line. The reference line region between the first time point t1 and the second time point t2 may be parallel to a bottom boundary line r of the frames 1500. That is, the reference line region between the first time point t1 and the second time point t2 may have an angle of 0° with respect to the bottom boundary line r of the frames 1500. The reference line region between the first time point t1 and the second time point t2 may be perpendicular relative to a side boundary line of the frames 1500.

The plurality of frames 1500 generated between the first time point t1 and the second time point t2 may be arranged to meet the first boundary line 1610. That is, a top boundary line of the plurality of frames 1500 generated between the first time point t1 and the second time point t2 may be arranged to meet the first boundary line 1610 of the panoramic image 1600. The top boundary line of the plurality of frames 1500 is arranged to meet the first boundary line 1610 of the panoramic image 1600, and therefore the dummy region 1650 is generated in a lower portion of the panoramic image 1600 which has a smaller width than that of the panoramic image 1600. The dummy region 1650 may be positioned between a lower portion of the frames 1500 and the second boundary line 1620.

A reference line region between the second time point t2 and the fourth time point t4 may be a curved line. The reference line region between the second time point t2 and the fourth time point t4 may have a plurality of angles with respect to the bottom boundary line r of the frames 1500. That is, the reference line region between the second time point t2 and the fourth time point t4 may have an angle that changes according to the time point.

In the reference line region at the third time point t3 between the second time point t2 and the fourth time point t4, a change amount of an absolute value of the corresponding angle may be changed with respect to the bottom boundary line r. That is, the change amount of the absolute value of an angle may have a positive value from the second time point t2 to the third time point t3, and have a negative value from the third time point t3 to the fourth time point t4. The absolute value of the angle of the reference line region may be increased from the second time point t2 to the third time point t3, and decreased from the third time point t3 to the fourth time point t4.

The plurality of frames 1500 generated between the second time point t2 and the fourth time point t4 may be arranged so as not to meet the first boundary line 1610 and the second boundary line 1620. Between the second time point t2 and the fourth time point t4, the dummy region 1650 may be generated between the first boundary line 1610 and an upper portion of the frames 1500, and generated between the second boundary line 1620 and the lower portion of the frames 1500.

A reference line region between the fourth time point t4 and the fifth time point t5 may be a straight line. The reference line region between the fourth time point t4 and the fifth time point t5 may be parallel to the bottom boundary line r of the frames 1500. That is, the reference line region between the fourth time point t4 and the fifth time point t5 may have an angle of 0° with respect to the bottom boundary line r of the frames 1500. The reference line region between the fourth time point t4 and the fifth time point t5 may be perpendicular to the side boundary line of the frames 1500. The reference line region between the fourth time point t4 and the fifth time point t5 may be parallel to the reference line region between the first time point t1 and the second time point t2.

The plurality of frames 1500 generated between the fourth time point t4 and the fifth time point t5 may be arranged to meet the second boundary line 1620. That is, a bottom boundary line of the plurality of frames 1500 generated between the fourth time point t4 and the fifth time point t5 may be arranged to meet the second boundary line 1620 of the panoramic image 1600. The bottom boundary line of the plurality of frames 1500 is arranged to meet the second boundary line 1620 of the panoramic image 1600 so that the dummy region 1650 may be generated in the upper portion of the panoramic image 1600 which has a smaller width than that of the panoramic image 1600. The dummy region 1650 may be positioned between the upper portion of the frames 1500 and the first boundary line 1610. The plurality of frames 1500 generated between the fourth time point t4 and the fifth time point t5 may be frames generated by imaging a lowest end of the object.

A reference line region between the fifth time point t5 and the seventh time point t7 may be a curved line. The reference line region between the fifth time point t5 and the seventh time point t7 may have a plurality of angles with respect to the bottom boundary line r of the frames 1500. That is, the reference line region between the fifth time point t5 and the seventh time point t7 may have an angle that is changed according to the time point.

In the reference line region at the sixth time point t6 between the fifth time point t5 and the seventh time point t7, a change amount of an absolute value of the corresponding angle may be changed with respect to the bottom boundary line r. That is, the change amount of the absolute value of an angle may have a positive value from the fifth time point t5 to the sixth time point t6, and have a negative value from the sixth time point t6 to the seventh time point t7. The absolute value of the angle of the reference line region may be increased from the fifth time point t5 to the sixth time point t6, and decreased from the sixth time point t6 to the seventh time point t7.

The plurality of frames 1500 generated between the fifth time point t5 and the seventh time point t7 may be arranged so as not to meet the first boundary line 1610 and the second boundary line 1620. Between the fifth time point t5 and the seventh time point t7, the dummy region 1650 may be generated between the first boundary line 1610 and the upper portion of the frames 1500, and generated between the second boundary line 1620 and the lower portion of the frames 1500.

The reference line region and dummy region 1650 between the fifth time point t5 and the seventh time point t7 may be symmetrical with the reference line region and dummy region 1650 between the second time point t2 and the fourth time point t4. The reference line region and dummy region 1650 between the fifth time point t5 and the seventh time point t7 may be bilaterally symmetrical with the reference line region and dummy region 1650 between the second time point t2 and the fourth time point t4 with respect to the middle region PM. The absolute value of the angle of the reference line region between the fifth time point t5 and the seventh time point t7 may be the same as the absolute value of the angle of the reference line region between the second time point t2 and the fourth time point t4.

A reference line region between the seventh time point t7 and the eighth time point t8 may be a straight line. The reference line region between the seventh time point t7 and the eighth time point t8 may be parallel to the bottom boundary line r of the frames 1500. That is, the reference line region between the seventh time point t7 and the eighth time point t8 may have an angle of 0° with respect to the bottom boundary line r of the frames 1500. The reference line region between the seventh time point t7 and the eighth time point t8 may be perpendicular relative to the side boundary line of the frames 1500. The reference line region between the seventh time point t7 and the eighth time point t8 may be parallel to the reference line region between the first time point t1 and the second time point t2. In addition, the reference line region between the seventh time point t7 and the eighth time point t8 may be parallel to the reference line region between the fourth time point t4 and the fifth time point t5.

The plurality of frames 1500 generated between the seventh time point t7 and the eighth time point t8 may be arranged to meet the first boundary line 1610. That is, a top boundary line of the plurality of frames 1500 generated between the seventh time point t7 and the eighth time point t8 may be arranged to meet the first boundary line 1610 of the panoramic image 1600. The top boundary line of the plurality of frames 1500 may be arranged to meet the first boundary line 1610 of the panoramic image 1600 so that the dummy region 1650 may be generated in the lower portion of the panoramic image 1600 which has a smaller width than that of the panoramic image 1600. The dummy region 1650 may be positioned between the lower portion of the frame 1500 and the second boundary line 1620.

The reference line region and dummy region 1650 between the seventh time point t7 and the eighth time point t8 may be symmetrical with the reference line region and dummy region 1650 between the first time point t1 and the second time point t2. The reference line region and dummy region 1650 between the seventh time point t7 and the eighth time point t8 may be bilaterally symmetrical with the reference line region and dummy region 1650 between the first time point t1 and the second time point t2 with respect to the middle region PM.

The panoramic image 1600 may have the reference line region and the dummy region 1650 which are symmetrical with each other with respect to the middle region PM.

—Overlapped Frame—

Figure 14A:
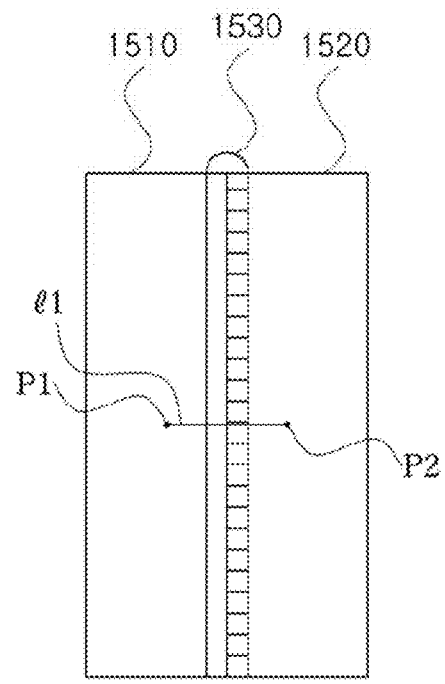
FIGS. 14A and 14B are enlarged views illustrating region A of FIG. 13.
Figure 14B:
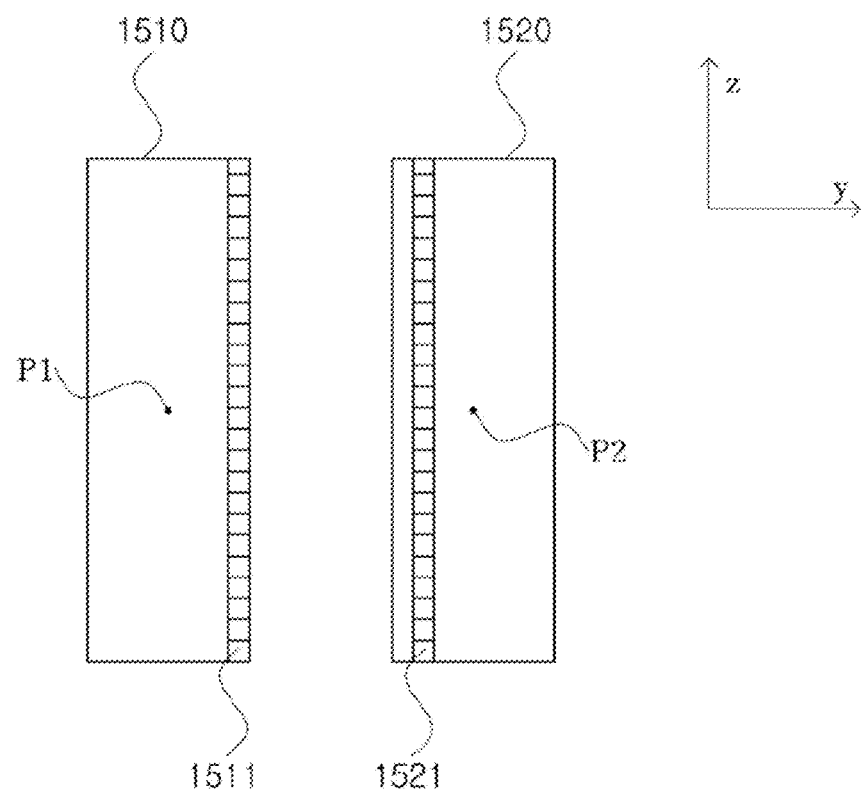
Figure 15A:
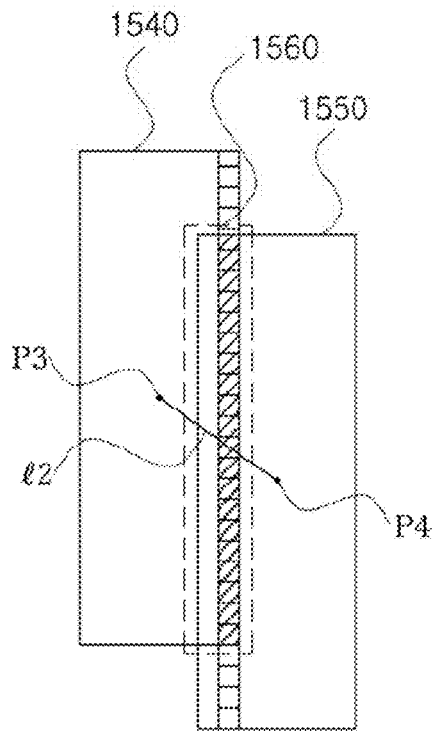
FIGS. 15A and 15B are enlarged views illustrating region B of FIG. 13.
Figure 15B:
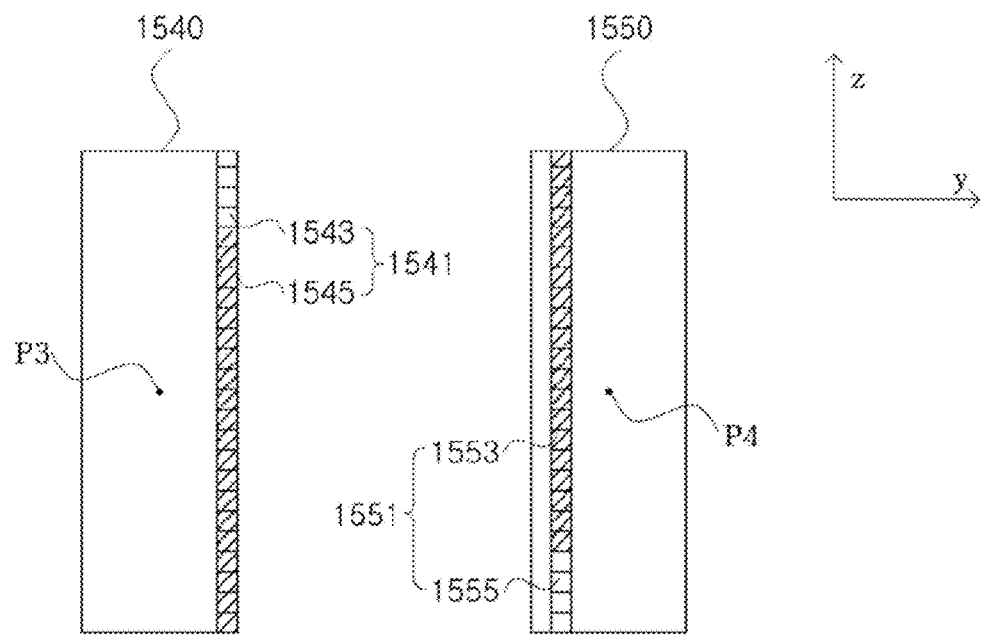

FIGS. 14A and 14B are enlarged views illustrating region A of FIG. 13, and FIGS. 15A and 15B are enlarged views illustrating region B of FIG. 13.

Referring to FIGS. 14A and 14B and FIG. 13, the X-ray detector 1400 may generate a first frame 1510 at a ninth time point t9 and generate a second frame 1520 at a tenth time point t10.

The ninth time point t9 and the tenth time point t10 may be arbitrary time points between the first time point t1 and the second time point t2. The ninth time point t9 and the tenth time point t10 may be adjacent time points. That is, the first frame 1510 and the second frame 1520 may be adjacent frames. However, as long as the first frame 1510 and the second frame 1520 can be overlapped with each other, the ninth time point t9 and the tenth time point t10 may be time points separated from each other rather than the adjacent time points.

The first frame 1510 and the second frame 1520 may have a plurality of pixels. The first frame 1510 and the second frame 1520 may be overlapped with each other to have a first overlapped region 1530. The first overlapped region 1530 may have a plurality of pixel columns. The first frame 1510 and the second frame 1520 may be overlapped with each other with respect to a first reference line l1. The first reference line l1 may be parallel to a lowest end of the first frame 1510.

The first frame 1510 and the second frame 1520 of the first overlapped region 1530 may be a region that is generated by detecting X-rays transmitted through the same region of the object. That is, the first overlapped region 1530 may be a region that is obtained by imaging the same region of the object. Pixels of the first overlapped region 1530 may have corresponding values. When a state of the X-ray detector 1400 generating the first frame 1510 is the same as a state of the X-ray detector 1400 generating the second frame 1520, the first frame 1510 and the second frame 1520 of the first overlapped region 1530 may have the same pixel values.

The first frame 1510 may have a first central point p1, and the second frame 1520 may have a second central point P2. The first central point P1 may be a center of gravity of the first frame 1510. The second central point P2 may be a center of gravity of the second frame 1520. The first central point P1 and the second central point P2 may be virtual points.

The first frame 1510 and the second frame 1520 may be arranged such that the first central point P1 and the second central point P2 are positioned on the first reference line l1. That is, the first reference line l1 may be a line connecting the first central point P1 and the second central point P2.

The first frame 1510 may include a plurality of pixel columns. The first frame 1510 may include an outermost pixel column 1511. The outermost pixel column 1511 may be a pixel column that is positioned in an outermost portion of the first frame 1510 adjacent to the second frame 1520. The outermost pixel column 1511 may be a pixel column included in the first overlapped region 1530.

The second frame 1520 may have a corresponding pixel column 1521 corresponding to the outermost pixel column 1511 of the first frame 1510. The outermost pixel column 1511 of the first frame 1510 and the corresponding pixel column 1521 of the second frame 1520 may be included in the first overlapped region 1530. The outermost pixel column 1511 and the corresponding pixel column 1521 may be overlapped with each other when the first frame 1510 and the second frame 1520 are overlapped with each other.

The outermost pixel column 1511 and the corresponding pixel column 1521 may be regions that are generated by detecting X-rays transmitted through the same region of the object. That is, the outermost pixel column 1511 and the corresponding pixel column 1521 may be regions that are obtained by imaging the same region of the object. Pixels of the outermost pixel column 1511 and pixels of the corresponding pixel column 1521 may have corresponding values. When the state of the X-ray detector 1400 generating the first frame 1510 is the same as the state of the X-ray detector 1400 generating the second frame 1520, the outermost pixel column 1511 and the corresponding pixel column 1521 may have the same pixel values.

An example in which the ninth time point t9 and the tenth time point t10 are time points between the first time point t1 and the second time point t2 has been described, but the ninth time point t9 and the tenth time point t10 may be time points between the fourth time point t4 and the fifth time point t5 or between the seventh time point t7 and the eighth time point t8.

Referring to FIG. 15 and FIG. 13, the X-ray detector 1400 may generate a third frame 1540 at an eleventh time point t11 and generate a fourth frame 1550 at a twelfth time point t12.

The eleventh time point t11 and the twelfth time point t12 may be arbitrary time points between the second time point t2 and the fourth time point t4. The eleventh time point t11 and the twelfth time point t12 may be adjacent time points. That is, the third frame 1540 and the fourth frame 1550 may be adjacent frames. However, as long as the third frame 1540 and the fourth frame 1550 can be overlapped with each other, the eleventh time point t11 and the twelfth time point t12 may be time points separated from each other rather than adjacent time points.

The third frame 1540 and the fourth frame 1550 may include a plurality of pixels. The third frame 1540 and the fourth frame 1550 may be overlapped with each other to have a second overlapped region 1560. The second overlapped region 1560 may include a plurality of pixel columns. The third frame 1540 and the fourth frame 1550 may be overlapped with each other with respect to a second reference line l2. The second reference line l2 may have an angle with respect to a lowest end of the third frame 1540. The second reference line l2 may not be parallel to the lowest end of the third frame 1540.

The third frame 1540 and fourth frame 1550 of the second overlapped region 1560 may be regions that are generated by detecting X-rays transmitted through the same region of the object. That is, the second overlapped region 1560 may be a region that is obtained by imaging the same region of the object. Pixels of the second overlapped region 1560 may have corresponding values. When a state of the X-ray detector 1400 generating the third frame 1540 is the same as a state of the X-ray detector 1400 generating the fourth frame 1550, the third frame 1540 and the fourth frame 1550 of the second overlapped region 1560 may have the same pixel values. The second overlapped region 1560 may have a smaller width than that of the third frame 1540. The second overlapped region 1560 may have a smaller width than that of the fourth frame 1550.

The third frame 1540 may have a third central point P3, and the fourth frame 1550 may have a fourth central point P4. The third central point P3 may be a center of gravity of the third frame 1540. The fourth central point P4 may be a center of gravity of the fourth frame 1550. The third central point P3 and the fourth central point P4 may be imaginary points.

The third frame 1540 and the fourth frame 1550 may be arranged such that the third central point P3 and the fourth central point P4 may be positioned on the second reference line l2. That is, the second reference line l2 may be a line connecting the third central point P3 and the fourth central point P4.

The third frame 1540 may include a plurality of pixel columns. The third frame 1540 may include an outermost pixel column 1541. The outermost pixel column 1541 may be a pixel column that is positioned in an outermost portion of the third frame 1540 adjacent to the fourth frame 1550.

The outermost pixel column 1541 may include a first pixel group 1543 and a second pixel group 1545. The first pixel group 1543 may include a part of the outermost pixel column 1541, and the second pixel group 1545 may include a part of the outermost pixel column 1541.

The first pixel group 1543 may include one or more pixels. The second pixel group 1545 may include one or more pixels. The first pixel group 1543 may be defined as pixels that are not included in the second overlapped region 1560. The second pixel group 1545 may be defined as pixels that are included in the second overlapped region 1560. The second pixel group 1545 may be positioned below the first pixel group 1543.

The fourth frame 1550 may include a pixel corresponding to one or more pixels of the second pixel group 1545 of the third frame 1540. The fourth frame 1550 may include a corresponding pixel group 1553 corresponding to each of a plurality of pixels of the second pixel group 1545 of the third frame 1540. The corresponding pixel group 1553 may be included in a corresponding pixel column 1551, and the corresponding pixel column 1551 may include the corresponding pixel group 1553 and a non-corresponding pixel group 1555. The non-corresponding pixel group 1555 does not correspond to the pixel column of the third frame 1540. The non-corresponding pixel group 1555 may be positioned below the corresponding pixel group 1553.

The second pixel group 1545 of the third frame 1540 and the corresponding pixel group 1553 may be included in the second overlapped region 1560. The second pixel group 1545 and the corresponding pixel group 1553 may be overlapped with each other when the third frame 1540 and the fourth frame 1550 are overlapped with each other.

The second pixel group 1545 and the corresponding pixel group 1553 may be regions that are generated by detecting X-rays transmitted through the same region of the object. That is, the second pixel group 1545 and the corresponding pixel group 1553 may be regions that are obtained by imaging the same region of the object. Pixels of the second pixel group 1545 and pixels of the corresponding pixel group 1553 may have corresponding values. When the state of the X-ray detector 1400 generating the third frame 1540 is the same as the state of the X-ray detector 1400 generating the fourth frame 1550, the second pixel group 1545 and the corresponding pixel group 1553 may have the same pixel values.

Since the second reference line l2 may have an angle without being parallel to a bottom boundary line of the third frame 1540, the third frame 1540 may be overlapped while not being matched in the Z-axis direction. That is, a top boundary line of the third frame 1540 and a top boundary line of the fourth frame 1550 are not formed as the same line and are overlapped with each other while being spaced apart from each other in the Z-axis direction. Accordingly, the fourth frame 1550 may include a pixel corresponding to one or more pixels of the second pixel group 1545, and does not include a pixel corresponding to the first pixel group 1543.

An example in which the eleventh time point t11 and the twelfth time point t12 are time points between the second time point t2 and the fourth time point t4 has been described, but the eleventh time point t11 and the twelfth time point t12 may be time points between the fifth time point t5 and the seventh time point t7. In this case, the second pixel group may be positioned above the first pixel group. That is, the third frame 1540 may be overlapped with the fourth frame 1550 by being shifted downward in the Z-axis direction thereof.

—Generated Actual Panoramic Image—

Figure 16:
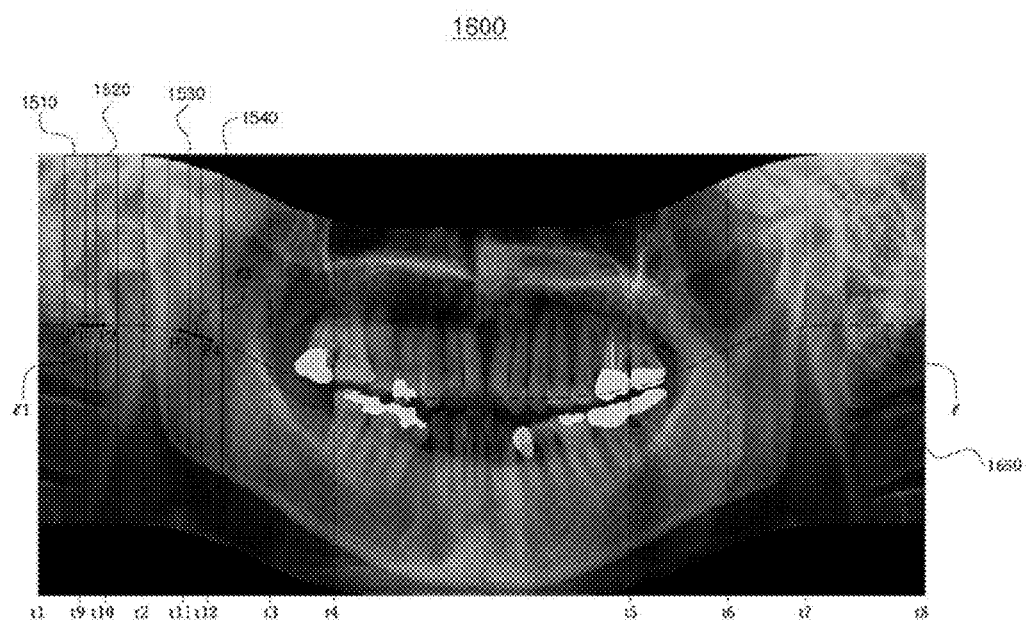
FIG. 16 is a view illustrating an actual panoramic image generated using an X-ray imaging apparatus according to an embodiment of the present invention.

FIG. 16 is a view illustrating an actual panoramic image generated using an X-ray imaging apparatus according to an embodiment of the present invention.

Referring to FIG. 16 and FIGS. 13 to 15, the X-ray imaging apparatus 1000 according to an embodiment of the present invention generates the panoramic image 1600.

The panoramic image 1600 may be generated by overlapping the plurality of frames 1500. The panoramic image 1600 may be configured such that the plurality of frames 1500 may be arranged from the first time point t1 to the eighth time point t8. The panoramic image may be configured such that the plurality of frames 1500 are overlapped and arranged along the reference line l.

The reference line l may be configured by connecting a plurality of reference lines. The reference line l may include the first reference line l1 and the second reference line l2. The reference line l may be a virtual line connecting the plurality of frames 1500. The reference line l may be a line connecting central points of the plurality of frames 1500. The central points may be centers of gravity of the frames 1500.

The first reference line l1 may be a line connecting the first frame 1510 at the ninth time point t9 and the second frame 1520 at the tenth time point t10. The first frame 1510 may include the first central point P1, and the second frame 1520 may include the second central point P2. The first reference line l1 may be a line connecting the first central point P1 and the second central point P2. The first frame 1510 and the second frame 1520 may be adjacent frames.

The second reference line l2 may be a line connecting the third frame 1540 at the eleventh time point t11 and the fourth frame 1550 at the twelfth time point t12. The third frame 1540 may include the third central point P3, and the fourth frame 1550 may include the fourth central point P4. The second reference line l2 may be a line connecting the third central point P3 and the fourth central point P4. The third frame 1540 and the fourth frame 1550 may be adjacent frames.

The first reference line l1 and the second reference line l2 may have different inclinations. The first reference line l1 and the second reference line l2 may meet at one point when extended, and the first reference line l1 and the second reference line l2 may form an acute angle when they meet at the one point.

The reference line l may be predefined according to the type of the object. The X-ray imaging apparatus 1000 according to an embodiment of the present invention may be used for imaging an overall structure of a tooth and an alveolar bone in a dental clinic, and therefore the reference line l may be predefined according to the type of the alveolar bone including a jaw of a patient that is the object. The reference line l may pass through a region of interest (ROI) of the jaw and alveolar bone of the patient to be imaged. That is, since the tooth and the alveolar bone may be a major ROI in a dental clinic, the reference line l may be preset so that it passes through at least a part of the tooth and alveolar bone.

The reference line l may include a region having an inclination by a structure of a typical jaw. In general, since a portion from a start of the jaw to the front of the jaw may have an inclination, the reference line l may be formed as an inclined region and since the front of the jaw does not have a large inclination, the reference line l may be also set to be parallel to a lower surface of the panoramic image 1600.

The reference line l may correspond to a movement path of the X-ray detector 1400. In addition, the reference line l may also correspond to an X-ray irradiation range of the X-ray generator 1300. Accordingly, by setting the reference line l so that it passes through the ROI and moving the X-ray detector 1400 and the X-ray irradiation range to image the ROI, it is possible to reduce an X-ray exposure dose. In other words, since the dummy region 1650 of the panoramic image 1600 is not irradiated with X-rays, it is possible to perform the same tooth diagnosis while reducing the X-ray exposure dose corresponding to the dummy region 1650. That is, it is possible to prevent an unnecessary region from being imaged in a process of imaging a tooth and an alveolar bone, thereby reducing the X-ray exposure dose.

In addition, since X-rays transmitted through a tooth and an alveolar bone may be detected by moving the X-ray detector 1400 linearly in a linear direction corresponding to a general shape of the tooth and the alveolar bone, the same result may be obtained using the X-ray detector 1400 having a smaller size compared to the prior art. Accordingly, it is possible to reduce manufacturing costs.

[Another Embodiment of X-ray Imaging Apparatus]

As to an X-ray imaging apparatus according to another embodiment, compared to the embodiments of FIGS. 1 to 16, an X-ray detector performs only a motion along an arc and an X-ray generator irradiates X-rays in a linear direction. Accordingly, in a description of the X-ray imaging apparatus according to another embodiment of the present invention, the same reference numerals are given to the same elements as those in FIGS. 1 to 16, and detailed descriptions thereof will be omitted.

—Movement of Light Receiving Area—

Hereinafter, a structure of the X-ray detector which is different from those in FIGS. 6 and 7 and moving of the light receiving area by the X-ray generator will be described.

Figure 17:
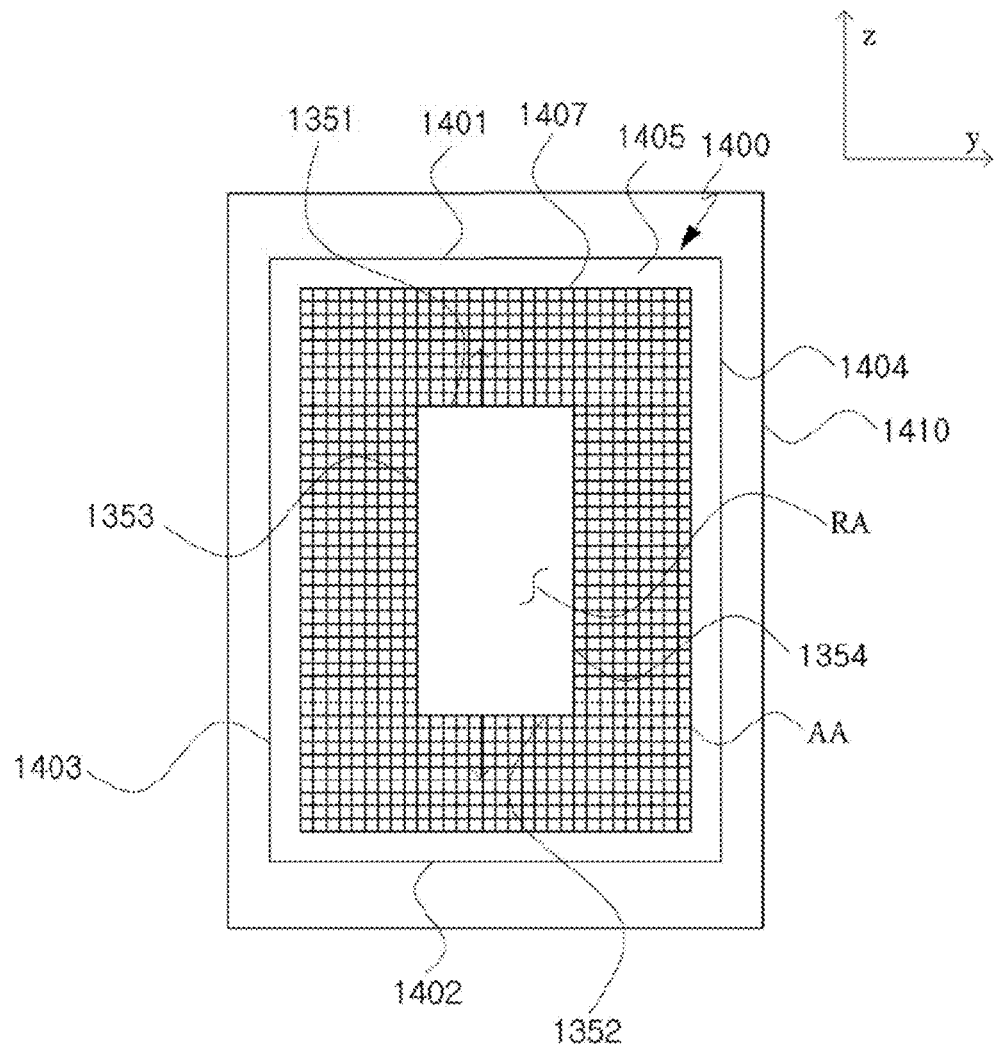
FIG. 17 is a view illustrating an X-ray detector according to another embodiment of the present invention.

FIG. 17 is a view illustrating an X-ray detector according to another embodiment of the present invention.

Referring to FIG. 17, the X-ray detector 1400 according to another embodiment of the present invention may be installed in the detector housing 1410. The X-ray detector 1400 may be installed to be in a state of being fixed to the detector housing 1410.

The X-ray detector 1400 may be formed in a rectangular shape. The X-ray detector 1400 may be formed in a rectangular shape. The X-ray detector 1400 may be formed in a rectangular shape such that the first boundary surface 1401 and the second boundary surface 1402 face each other and the third boundary surface 1403 and the fourth boundary surface 1404 face each other. The first boundary surface 1401 may have the same length as the second boundary surface 1402, and the third boundary surface 1403 may have the same length as the fourth boundary surface 1404. The first boundary surface 1401 may have a length shorter than that of the third boundary surface 1403.

The X-ray detector 1400 may have a square shape. The X-ray detector 1400 may be used for CT.

The X-ray detector 1400 may include a plurality of pixels 1407 positioned on the detector body 1405.

The light receiving area RA may be defined on the X-ray detector 1400. The light receiving area RA may be an area of receiving X-rays. The light receiving area RA may be located on the plurality of pixels 1407. The light receiving area RA may be moved by the X-ray generator 1300. The light receiving area RA may be moved such that a path of the X-rays is restricted by the optical path restricting unit 1330 of the X-ray generator 1300. For a description of the optical path restricting unit 1330, refer to the above-described structure of the X-ray generator 1300.

The light receiving area RA may include a first side 1351 adjacent to the first boundary surface 1401, a second side 1352 facing the first side 1351, and a third side 1353 and a fourth side 1354 connecting the first side 1351 and the second side 1352. The second side 1352 may be an end of the light receiving area RA adjacent to the second boundary surface 1402, the third side 1353 may be an end of the light receiving area RA adjacent to the third boundary surface 1403, and the fourth side 1354 may be an end of the light receiving area RA adjacent to the fourth boundary surface 1404.

The light receiving area RA may have an area smaller than that of the X-ray detector 1400.

The light receiving area RA may have a smaller size than that of an active area AA in which the pixels 1407 of the X-ray detector 1400 are positioned. Alternatively, the light receiving area RA may have a smaller width than that of the active area AA but have a long length. The width of the light receiving area RA may be defined as the length of the first side 1351, and the length of the light receiving area RA may be defined as the length of the third side 1353.

The light receiving area RA may be moved in a Z-axis direction. The light receiving area RA may be moved in a direction parallel to the third side 1353. The light receiving area RA may perform a linear motion in the Z-axis direction. The linear motion may include a first linear motion and a second linear motion.

A movement in a direction of the second side 1352 of the light receiving area RA may be defined as the first linear motion, and a movement in a direction of the first side 1351 may be defined as the second linear motion. The light receiving area RA may perform a reciprocating motion including the first linear motion and the second linear motion by the optical path restricting unit 1330.

By the first linear motion, the first side 1351 of the light receiving area RA and the first boundary surface 1401 of the X-ray detector 1400 may move away from each other and the second side 1352 of the light receiving area RA and the second boundary surface 1402 of the X-ray detector 1400 may approach each other. In addition, by the second linear motion, the first side 1351 of the light receiving area RA and the first boundary surface 1401 of the X-ray detector 1400 may approach each other and the second side 1352 of the light receiving area RA and the second boundary surface 1402 of the X-ray detector 1400 may move away from each other.

A limiting surface of the first linear motion of the light receiving area RA may be the second boundary surface 1402. In addition, a limiting surface of the second linear motion of the light receiving area RA may be the first boundary surface 1401. That is, the light receiving area RA may not be moved to the outside of the X-ray detector 1400. By controlling the optical path restricting unit 1330 so as to restrict the movement of the light receiving area RA to the outside of the X-ray detector 1400, it is possible to prevent external exposure by X-rays.

In addition, the light receiving area RA during a previous exposure period may be set to be different from the light receiving area RA during a current exposure period. That is, the light receiving area at a specific time point during the current exposure period may be set to be different from the light receiving area at the specific time point during the previous exposure period.

By setting the light receiving area RA differently during the exposure period, it is possible to prevent the degradation of the X-ray generator and improve the reliability of the panoramic image.

The light receiving area RA may be moved linearly in a linear direction having an angle with respect to an arc drawn by the X-ray generator 1300 in the same manner as the X-ray detector of FIG. 9.

—Imaging of Object—

Figure 18:
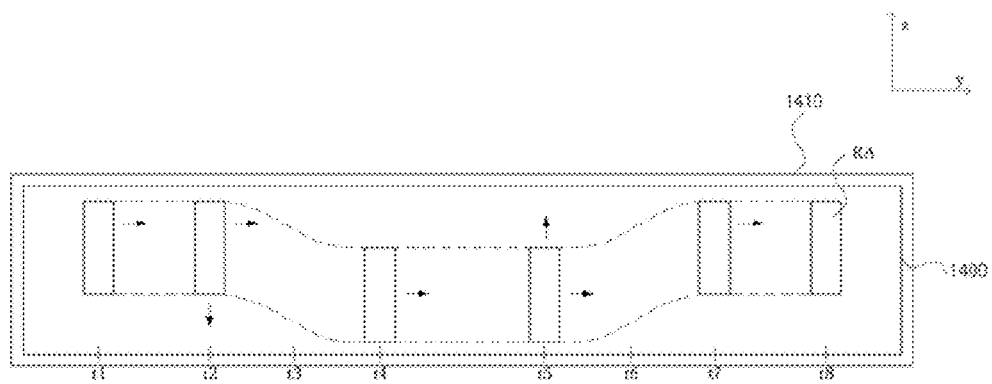
FIG. 18 is a view illustrating a movement path of a light receiving area according to another embodiment of the present invention.

FIG. 18 is a view illustrating a movement path of a light receiving area according to another embodiment of the present invention.

The movement path of the light receiving area according to another embodiment of the present invention is similar to the movement path of the X-ray detector of FIG. 11, and therefore detailed descriptions of elements which are the same as those in FIG. 11 will be omitted.

Referring to FIG. 18, the light receiving area RA according to another embodiment of the present invention may be moved on the X-ray detector 1400.

In the drawing, the X-ray detector 1400 and the detector housing 1410 are shown to be formed integrally, but the movement of the X-ray detector 1400 and the detector housing 1410 is shown successively over time. In addition, in the drawing, six light receiving areas RA are shown, but positions at a specific time point of the light receiving area RA that is moved successively is shown.

The light receiving area RA may start to be moved at the first time point t1 and stop being moved at the eighth time point t8. The light receiving area RA may be moved along the movement path during the first time point t to the eighth time point t8. The controller 1100 may move the light receiving area RA by controlling the optical path restricting unit 1330 of the X-ray generator 1300.

The light receiving area RA may perform the linear motion dining a period from the second time point t2 to the seventh time point t7 while maintaining the motion to draw the arc on the X-ray detector 1400.

The light receiving area RA may perform the first linear motion during a period from the second time point t2 to the fourth time point t4, and perform the second linear motion during a period from the fifth time point t5 to the seventh time point t7.

The light receiving area RA at the second time point t2 is located at a first position. The first position may be a position at which the first side 1351 of the light receiving area RA and the first boundary surface 1401 of the X-ray detector 1400 are adjacent to each other. At this point, a distance between the first side 1351 and the first boundary surface 1401 may be smaller than a distance between the second side 1352 and the second boundary surface 1402.

When the light receiving area RA performs the linear motion during the period from the second time point t2 to the fourth time point t4, the light receiving area RA may be moved in a direction of the second boundary surface 1402. During the period from the second time point t2 to the fourth time point t4, the distance between the first side 1351 and the first boundary surface 1401 may be increased and the distance between the second side 1352 and the second boundary surface 1402 may be decreased. A time point when the distance between the first side 1351 and the first boundary surface 1401 and the distance between the second side 1352 and the second boundary surface 1402 are the same may be the third time point t3.

The light receiving area RA may reach a second position at the fourth time point t4 by the first linear motion. The second position may be a position at which the second side 1352 of the light receiving area RA and the second boundary surface 1402 of the X-ray detector 1400 are adjacent to each other. At this point, the distance between the first side 1351 and the first boundary surface 1401 may be larger than the distance between the second side 1352 and the second boundary surface 1402.

When the light receiving area RA performs the linear motion during a period from the fifth time point t5 to the seventh time point t7, the light receiving area RA may be moved in a direction of the first boundary surface 1401. During the period from the fifth time point t5 to the seventh time point t7, the distance between the first side 1351 and the first boundary surface 1401 may be decreased and the distance between the second side 1352 and the second boundary surface 1402 may be increased. A time point when the distance between the first side 1351 and the first boundary surface 1401 and the distance between the second side 1352 and the second boundary surface 1402 are the same may be the third time point t3.

The light receiving area RA may reach the first position at the seventh time point t7 by the second linear motion.

A process of generating a frame and generating a panoramic image according to another embodiment of the present invention is the same as that in FIGS. 12 to 16. The X-ray imaging apparatus according to another embodiment of the present invention may move the light receiving area RA irradiated with X-rays and generate a panoramic image, thereby reducing an X-ray exposure dose. In particular, the exposure dose may be reduced by moving the light receiving area instead of a separate structure that moves the X-ray detector, thereby reducing manufacturing costs which may be generated when the separate structure used for the movement of the X-ray detector is mounted.

Although not shown, according to another embodiment of the present invention, a mode may be set. The mode may include a first mode and a second mode. When the first mode is set, the X-ray detector 1400 may perform the linear motion during a partial period, and when the second mode is set, the X-ray detector 1400 may perform only the motion along the arc having a radius of curvature within a range without the linear motion.

As described above, the X-ray imaging apparatus according to the embodiments of the present invention may reduce the X-ray irradiation range exposed to the object, thereby reducing the X-ray exposure dose.

The method for generating a panoramic image according to the embodiments of the present invention may generate a panoramic image using a relatively small X-ray detector, thereby reducing manufacturing costs.

It should be apparent to those skilled in the art that various modifications can be made to the above-described exemplary embodiments of the present invention without departing from the spirit or scope of the invention. Thus, the present invention is intended to cover all such modifications provided they come within the scope of the appended claims and their equivalents.

What is claimed is:

1. An X-ray imaging apparatus comprising:
    an X-ray generator that irradiates an object with X-rays during an exposure period;
    an X-ray detector that detects X-rays transmitted through the object; and
    a movement unit that moves the X-ray generator and the X-ray detector,
    wherein the X-ray generator is moved along an arc having a radius of curvature within a range with respect to a rotational axis, wherein the motion along the arc starts at a first point and ends at a second point,
    wherein the X-ray detector is moved in a linear direction having an angle with respect to a plane of the arc during at least a partial period of a period between the first point and the second point,
    wherein the motion in a linear direction starts at a third that is the same as or later than the first point and ends at a fourth point that is the same as or earlier than the second point,
    a first difference between the first point and the second point is larger than or equal to a second difference between the third point and the fourth point,
    wherein the linear motion of the X-ray detector is a reciprocating motion between a first position and a second position,
    wherein the X-ray detector is moved from the first position to the second position during a first linear motion, the linear motion being started at the third point and being ended at a fifth point, and
    wherein the X-ray detector is moved from the second position to the first position during a second linear motion, the second linear motion being started at a sixth point and being ended at the fourth point.

2. The X-ray imaging apparatus of claim 1, wherein the X-ray detector is used for computed tomography (CT).

3. The X-ray imaging apparatus of claim 1, wherein the fifth point and the sixth point are the same point.

4. The X-ray imaging apparatus of claim 1, wherein the X-ray detector is located at the second position between the fifth point and the sixth point, and detects X-rays transmitted through a lowest end of a region of interest between the fifth point and the sixth point.

5. The X-ray imaging apparatus of claim 1, wherein the X-ray generator is moved in a linear direction between the third point and the fourth point.

6. The X-ray imaging apparatus of claim 1, further comprising:
    a path restricting unit that is located between the X-ray generator and the object and restricts an X-ray irradiation range from the X-ray generator so that the X-rays are controlled to be output toward a specific region of the object.

7. The X-ray imaging apparatus of claim 6, wherein the path restricting unit controls a light receiving area to be moved in a linear direction between the third point and the fourth point.

8. The X-ray imaging apparatus of claim 1, further comprising:
    a detector housing in which the X-ray detector is located, wherein the X-ray detector is moved in a linear motion by a linear motion of the detector housing.

9. The X-ray imaging apparatus of claim 8, further comprising:
    a linear movement unit that linearly moves the detector housing.

10. An X-ray imaging apparatus comprising:
    an X-ray generator that generates X-rays during an exposure period;
    a path restricting unit that restricts an X-ray irradiation range from the X-ray generator;
    an X-ray detector that includes a light receiving area, wherein the light receiving area is determined an area of receiving X-rays transmitted through the object; and
    a movement unit that moves the X-ray generator and the X-ray detector,
    wherein the X-ray generator is moved along an arc having a radius of curvature within a range, wherein a motion along the arc starts at a first point and ends at a second point,
    wherein the light receiving area is moved in a linear direction having an angle with respect to a plane of the arc during at least a partial period of a period between the first point and the second point, wherein the motion in a linear direction starts at a third point that is the same as or later than the first point and ends at a fourth point that is the same as or earlier than the second point, and a first difference between the first point and the second point is larger than or equal to a second difference between the third point and the fourth point, wherein the linear motion of the X-ray detector is a reciprocating motion between a first position and a second position, wherein the X-ray detector is moved from the first position to the second position during a first linear motion, the linear motion being started at the third point and being ended at a fifth point, and wherein the X-ray detector is moved from the second position to the first position during a second linear motion, the second linear motion being started at a sixth point and being ended at the fourth point.

11. The X-ray imaging apparatus of claim 10, wherein the X-ray detector includes a first boundary surface and a second boundary surface facing each other in a linear movement axis, wherein a distance between a first side of the light receiving area adjacent to the first boundary surface and the first boundary surface is smaller than a distance between a second side of the light receiving area adjacent to the second boundary surface and the second boundary surface during the first point to the third point, and wherein the first side of the light receiving area is an end of the light receiving area adjacent to the first boundary surface, and the second side of the light receiving area is an end of the light receiving area adjacent to the second boundary surface.

12. The X-ray imaging apparatus of claim 10, wherein the X-ray detector includes a first boundary surface and a second boundary surface facing each other in a linear movement axis, wherein a distance between a first side of the light receiving area adjacent to the first boundary surface and the first boundary surface is larger than a distance between a second side of the light receiving area adjacent to the second boundary surface and the second boundary surface during a partial period between the third point and the fourth point, and wherein the first side of the light receiving area is an end of the light receiving area adjacent to the first boundary surface, and the second side of the light receiving area is an end of the light receiving area adjacent to the second boundary surface.

13. The X-ray imaging apparatus of claim 10, wherein the motion in the linear direction of the light receiving area is a reciprocating motion between a first position and a second position.

14. The X-ray imaging apparatus of claim 13, wherein the light receiving area is moved from the first position to the second position during a first linear motion, the first linear motion being started at the third point and being ended at a fifth point, wherein the light receiving area is moved from the second position to the first position during a second linear motion, the second linear motion being started at a sixth point and being ended at a fourth point.

15. The X-ray imaging apparatus of claim 14, wherein the X-ray detector includes a first boundary surface and a second boundary surface facing each other in a linear movement axis, wherein a distance between a first side of the light receiving area adjacent to the first boundary surface and the first boundary surface is increased and a distance between a second side of the light receiving area adjacent to the second boundary surface and the second boundary surface is decreased during the third point to the fifth point, and wherein the first side of the light receiving area is an end of the light receiving area adjacent to the first boundary surface, and the second side of the light receiving area is an end of the light receiving area adjacent to the second boundary surface.

16. The X-ray imaging apparatus of claim 14, wherein the X-ray detector includes a first boundary surface and a second boundary surface facing each other in a linear movement axis, wherein a distance between a first side of the light receiving area adjacent to the first boundary surface and the first boundary surface is decreased and a distance between a second side of the light receiving area adjacent to the second boundary surface and the second boundary surface is increased during the sixth point to the fourth point, and wherein the first side of the light receiving area is an end of the light receiving area adjacent to the first boundary surface, and the second side of the light receiving area is an end of the light receiving area adjacent to the second boundary surface.

17. The X-ray imaging apparatus of claim 10, wherein the light receiving area at a specific point during the exposure period is set to be different from the light receiving area at the specific point during a previous exposure period.

* * * * *